US008425784B2

(12) United States Patent
Subramaniam et al.

(10) Patent No.: US 8,425,784 B2
(45) Date of Patent: Apr. 23, 2013

(54) OZONOLYSIS REACTIONS IN LIQUID $CO_2$ AND $CO_2$-EXPANDED SOLVENTS

(75) Inventors: Bala Subramaniam, Lawrence, KS (US); Daryle Busch, Lawrence, KS (US); Andrew M. Danby, Lawrence, KS (US); Thomas P. Binder, Decatur, IL (US)

(73) Assignees: University of Kansas, Lawrence, KS (US); Archer Daniels Midland Company, Decatur, IL (US)

( * ) Notice: Subject to any disclaimer, the term of this patent is extended or adjusted under 35 U.S.C. 154(b) by 865 days.

(21) Appl. No.: 12/264,446

(22) Filed: Nov. 4, 2008

(65) Prior Publication Data

US 2009/0118498 A1 May 7, 2009

Related U.S. Application Data

(60) Provisional application No. 60/985,407, filed on Nov. 5, 2007.

(51) Int. Cl.
*C02F 1/78* (2006.01)

(52) U.S. Cl.
USPC ........... 210/760; 210/766; 210/908; 210/910; 544/47; 560/177; 560/129; 549/277; 562/110

(58) Field of Classification Search .................. 210/760, 210/908–910, 766; 544/47; 560/177, 129; 549/277; 562/110
See application file for complete search history.

(56) References Cited

U.S. PATENT DOCUMENTS

| 6,448,454 | B1 * | 9/2002 | Subramaniam et al. ...... 568/800 |
| 7,219,677 | B1 | 5/2007 | Jackson |
| 2003/0146310 | A1 * | 8/2003 | Jackson ........................ 239/690 |
| 2004/0033269 | A1 | 2/2004 | Hei et al. |
| 2005/0274125 | A1 | 12/2005 | Giacobbe |
| 2007/0062372 | A1 | 3/2007 | Jain |

FOREIGN PATENT DOCUMENTS

| JP | H11-347413 | 12/1999 |
| JP | 2007-210881 | 8/2007 |

OTHER PUBLICATIONS

El-Din et al. "Oxidation of resin and fatty acid by ozone: Kinetics and toxicity study" Water research 40 (Jan. 2006) 392-400.*

(Continued)

*Primary Examiner* — Lucas Stelling
(74) *Attorney, Agent, or Firm* — Stinson Morrison Hecker LLP

(57) ABSTRACT

A method for increasing ozone concentration in a liquid can include: providing a gas having ozone; introducing the ozone-containing gas into a liquid, wherein the liquid and ozone combination has a temperature between about 0.8 and about 1.5 times the critical temperature of ozone; and increasing isothermally, the pressure of the ozone-containing gas above the liquid to about 0.3 to about 5 times the critical pressure of ozone so as to increase the ozone concentration in the liquid. The temperature is expressed in absolute units (Kelvin or Rankin). The method can be used for removing ozone from a gas or for purifying ozone. The liquid having a high ozone concentration can be used for ozonolysis of a substrate.

27 Claims, 15 Drawing Sheets

OTHER PUBLICATIONS

Baber et al. "Application of Catalytic Ozone Chemistry for Improving Biodiesel Product Performance" Miomacromolecules 2005, 6 (3), 1334-1344.*

Kang et al.; The Kinetics of the Sonochemical Process for the Destruction of Aliphatic and Aromatic Hydrocarbons; Korean Journal of Chemical Engineering; 2001; 18(3), pp. 336-341; Korea.

Kirk-Othmer; Dicarboxylic Acids; Encyclopedia of Chemical Technology 4$^{th}$ Edition,; 1996; vol. 8; pp. 124-125; John Wiley & Sons; New York, USA.

Musie, Ghezai et al.; "Catalytic oxidations in carbon dioxide-based reaction media, including novel $CO_2$-expanded phases," Coordination Chemistry Reviews.; 2001; pp. 219-221, 789-820; USA.

Wei, Ming, et al.;,"CO-Expanded Solvents: Unique and Versatile Media for Performing Homogeneous Catalytic Oxidations," JACS—Journal of the American Chemical Society; 2002; 124 (11), pp. 2513-2517; Washington D.C., USA.

* cited by examiner

Azelaic Acid Me Ester      Nonanoic Acid

2-Indanone

| | 1st order rate constant, $k_0$ | |
|---|---|---|
| Solvent | No ultrasound | With ultrasound |
| Water [†] | | $4.7 \times 10^{-3}$ s$^{-1}$ |
| $CO_2$ [‡] | $3.3(5) \times 10^{-5}$ s$^{-1}$ | $5.0(2) \times 10^{-5}$ s$^{-1}$ |

[†] pH = 4.6, T = 24 ± 2 °C, 360W / L
[‡] T = -1.2 ± 0.5 °C, 383 W / L

OZONOLYSIS REACTIONS IN LIQUID $CO_2$ AND $CO_2$-EXPANDED SOLVENTS

CROSS-REFERENCE TO RELATED APPLICATIONS

The present invention claims the benefit of U.S. Provisional Application Ser. No. 60/985,407, filed Nov. 5, 2007, which application is incorporated herein by specific reference in their entirety.

BACKGROUND

Ozonolysis reactions have been traditionally performed by bubbling $O_3$ through either an aqueous phase or an organic liquid phase containing a substrate to be chemically modified, such as molecules containing carbon-carbon double bonds (i.e., C=C). The conventional methods, however, have several drawbacks. Firstly, since $O_3$ is highly reactive, the reaction temperatures employed are typically sub-ambient (often around 0° C.), wherein the $O_3$ solubility in the liquid phase is low albeit typically greater than the solubility of dioxygen. For example, the $O_3$ solubility in water is $0.105 \times 10^{-2}$ g/mL at 0° C. and 1.013 bar pressure. Secondly, the $O_3$ reacts with many traditional organic solvents, which not only decreases $O_3$ availability for oxidizing the substrate, but also results in the formation of undesired products (e.g., waste) arising from solvent oxidation and increased solvent usage. Thirdly, the $O_3$ solubility in the liquid phase is not sensitively tunable with pressure, which often limits the ability to control reaction rate and product selectivity.

Thus, it would be beneficial to have a process and reaction conditions for performing ozonolysis with increased $O_3$ solubility in the solvent. Additionally, it would be beneficial to have a process and reaction conditions for performing ozonolysis in a solvent that is substantially inert with respect to $O_3$ so as to limit the number and amount of unfavorable side products. Further, it would be beneficial to have a process and reaction conditions for performing ozonolysis where the $O_3$ solubility in the liquid phase is tunable with pressure so as to provide the ability to control reaction rate and product selectivity.

SUMMARY

In one embodiment, the present invention includes a method for increasing ozone concentration in a liquid. Such a method can include: providing a gas having ozone; introducing the ozone-containing gas into a liquid, wherein the liquid and ozone combination has a temperature between about 0.8 and about 1.5 times the critical temperature of ozone; and increasing isothermally, the pressure of the ozone-containing gas above the liquid to about 0.3 to about 5 times the critical pressure of ozone so as to increase the ozone concentration in the liquid. Also, the temperature can be between about 1 to about 1.2 times the critical temperature of ozone, wherein the temperature is expressed in Kelvin. Additionally, the pressure can be increased to about 0.5 to about 2 times the critical pressure of ozone, wherein the pressure is expressed in bars. The ozone concentration in the liquid is increased at least about 5 times, above half an order of magnitude, or to about an order of magnitude higher. Of course, the temperature and pressure ranges can be converted and expressed in other units.

In one embodiment, the liquid can include any of liquid carbon dioxide, liquid light hydrocarbons (e.g., $C_4$ or less), methanol, ethanol, alcohols, hexane, liquid $SF_6$, liquid xenon, water, fluorocarbon solvents, highly oxygenated molecules, highly fluorinated molecules, $CF_3CO_2H$, ionic liquids, strong liquid acids, $H_2SO_4$, $HSO_3F$, $HSO_3CF_3$, organic acids, saturated hydrocarbons, or combinations thereof. Also, the liquid can be a carbon dioxide expanded liquid of the foregoing liquids.

In one embodiment, the present invention can include a method for extracting ozone from a gas. Such a method can include: providing a gas having ozone at a temperature between about 0.8 and about 1.5 times the critical temperature of ozone; increasing isothermally, the pressure of the ozone to about 0.3 to about 5 times the critical pressure of ozone; and introducing the compressed ozone into a liquid, wherein the liquid and ozone combination has a temperature between about 0.8 and about 1.5 times the critical temperature of ozone and the pressure of the liquid and ozone combination is about 0.3 to about 5 times the critical pressure of ozone. The temperature and pressures can be as described herein. Also, the liquids and carbon dioxide expanded liquids can be as described herein.

In one embodiment, the present invention can include a method of performing ozonolysis on a molecule in a liquid. Such a method can include: providing a composition having a liquid and ozone, wherein the liquid and ozone composition has a temperature between about 1 to about 1.2 times the critical temperature of ozone and a pressure between about 0.5 to about 2 times the critical pressure of ozone, wherein the molecule is dissolved or dispersed in the liquid; and reacting the molecule with the ozone. The method can further include introducing the molecule into one of the following: the liquid before the ozone; the ozone before the liquid; or the liquid and ozone combination. The temperature and pressures can be as described herein. Also, the liquids and carbon dioxide expanded liquids can be as described herein.

In one embodiment, the ozonolysis can further include: introducing the ozone into the liquid, wherein the liquid and ozone combination has a temperature between about 0.8 and about 1.5 times the critical temperature of ozone; and increasing, isothermally, the pressure of the ozone in the liquid to about 0.3 to about 5 times the critical pressure of ozone so as to increase the ozone concentration in the liquid.

In one embodiment, the molecule undergoing ozonolysis can be selected from the group consisting of a molecule having an unsaturated hydrocarbon, a molecule having a carbon-carbon double bond, unsaturated hydrocarbon acids, methyl oleate, oils, fats, soybean oil, unsaturated fatty acids, vegetable fatty acids, esters of fatty acids, fatty acid amides, alkenes, steroids, benzylics, a molecule having an allylic moiety, terpenes, cephalosporin, cephalosporin derivatives, a tertiary allylic alcohol, and the like.

In one embodiment, the present invention can include a fluid composition for performing ozonolysis on a molecule that has a combination of a liquid, such as liquid carbon dioxide or a carbon dioxide expanded liquid, and ozone having a temperature between about 1 to about 1.2 times the critical temperature of ozone and a pressure between about 0.5 to about 2 times the critical pressure of ozone. The composition can also include the molecule undergoing ozonolysis. The temperature and pressures can be as described herein. Also, the liquids and carbon dioxide expanded liquids can be as described herein.

In one embodiment, the fluid composition can be characterized by having an absorption band at $\lambda_{max}$ at about 253.7 nm and at about 577 nm and 603 nm, wherein at least one of the $\lambda_{max}$ has an absorbance unit of about 0.005 units when the pressure is below about 0.5 times the critical pressure of ozone and the $\lambda_{max}$ has an absorbance unit of about 0.01 to about 0.1 when the pressure is between about 0.5 to about 2 times the critical pressure of ozone.

In one embodiment, the present invention can include a method for separating ozone from air or an oxygen gas having the ozone. Such a method can include: providing a gas comprising ozone having a temperature above the critical temperature of ozone and a pressure below the critical pressure of ozone; changing the temperature of the gas to a temperature to about or less than the critical temperature of ozone; and increasing the pressure of the gas to about the critical pressure of ozone so as to separate the ozone from the gas. The temperature and pressures can be as described herein. Also, the liquids and carbon dioxide expanded liquids can be as described herein. Optionally, the gas is in the presence of a liquid and the ozone separates from the gas into the liquid.

These and other embodiments and features of the sensor device will become more fully apparent from the following description and appended claims, or may be learned by the practice of the sensor device as set forth hereinafter.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

To further clarify the above and other advantages and features of the ozonolysis reactor device and compositions of the feed and reaction mixtures, an illustrative description of the ozonolysis reactor device will be rendered by reference to the appended drawings. It is appreciated that these drawings depict only illustrated embodiments of the ozonolysis reactor device and are therefore not to be considered limiting of its scope. As such, the figures should not be construed to be limiting any object in shape or size and the features of the present invention, such as the ozonolysis reactor device, can have various shapes and sizes as needed or determined.

DETAILED DESCRIPTION

Figure 1A:
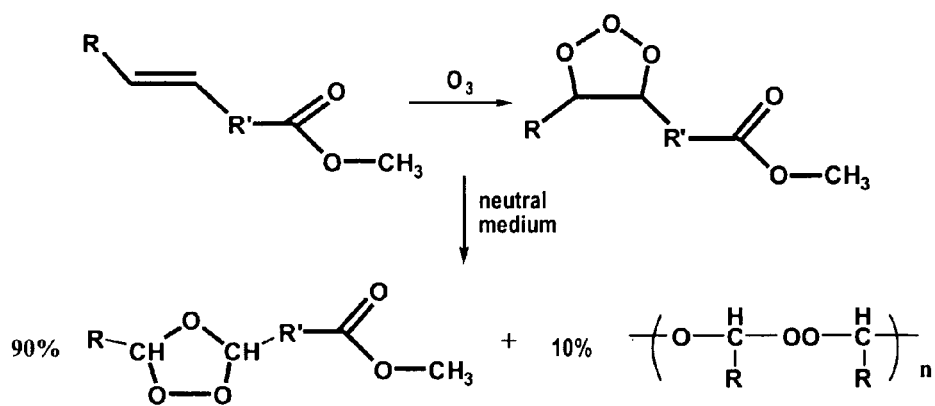
FIGS. 1A-1C are schematic representations of ozonolysis reactions (*Kirk-Othmer Encyclopedia of Chemical Technology* 4th Edition, John Wiley and Sons, New York 8 124-125 (1996)).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

I. Introduction

Generally, the present invention includes novel processes for increasing ozone concentrations in liquids and for performing ozonolysis reactions. Ozone has a critical temperature ($T_c$) of −12.15° C. (261 K), a critical pressure ($P_c$) of 55.73 bar (CHECK), and a critical density ($\rho_c$) of 540 kg/m³. In the ozonolysis process, the substrate (e.g., molecule containing C═C) is either dissolved or emulsified in liquid carbon dioxide or carbon dioxide-expanded solvents. In order to increase ozone concentrations in liquids, ozone ($O_3$) containing gas stream, produced using either air or oxygen in an ozone generator, is added to the liquid phase (e.g., liquid carbon or carbon dioxide-expanded solvents) at temperatures preferably between about 1-1.2 times the critical temperature of $O_3$ (expressed in K). The ozone is compressed to pressures preferably between about 0.5-2 times the critical pressure of $O_3$. Solubility of $O_3$ in liquid $CO_2$ has been determined to increase by nearly an order of magnitude when the pressure is increased from approximately 51 to 65 bar. Under these conditions, it has been shown that the $O_3$ is stable when mixed with liquid $CO_2$, and the $O_3$ can cleave carbon-carbon double bonds in substrates, especially such as those in the context of the bio-refinery, producing building blocks for synthesis of a variety of industrial chemicals. The reaction proceeds via intermediates that are meta-stable, but further oxidation or reduction subsequent to the primary ozone oxidation produces molecules of lower mass, which are commonly suitable as building blocks for chemical synthesis. As an example, it has now been shown that ozonolysis of methyl oleate, $CH_3(CH_2)_7CH=CH(CH_2)_7C(=O)OCH_3$, in liquid $CO_2$ and $CO_2$-expanded liquids, produces carboxylic acids, dicarboxylic acids, and aldehydes.

The ozonolysis process of the present invention may be employed to cleave carbon-carbon double bonds in substrates, especially such as those in the context of the biorefinery, producing building blocks for synthesis of a variety of industrial chemicals. The reaction proceeds via intermediates that are meta-stable, but further oxidation or reduction subsequent to the primary ozone oxidation produces molecules of lower mass, suitable as building blocks for chemical synthesis. In liquid $CO_2$, ozone density increases significantly close to its critical point, which allows for increasing the solubility of ozone and the capability of tuning the ozone concentration in the liquid phase for a particular purpose. Also, ozone preferentially oxidizes many olefinic substrates in $CO_2$ and CXL. For methyl oleate ozonation, the solvent system produces the following: In $CO_2$, nonanal, nonanoic acid, and nonanedoic acid are produced; In $CO_2$ expanded hexane, nonanol, nonanoic acid, nonanedoic acid are produced; and in $CO_2$ expanded methanol, nonanedoic acid and nonanoic acid are produced.

The significant characteristics of the new process are as follows: (i) The $O_3$ is stable in the preferred solvent due to its non-reactivity at preferred reaction conditions; (ii) At the preferred reaction temperatures, the $O_3$ solubility in the solvent may be increased by about an order of magnitude with relatively small changes in pressure. This tunability provides an ability to control reaction rates and product selectivity; (iii) Reduced flammability hazards; (iv) Low toxicity of solvent; (v) Facile product separation.

Figure 1B:
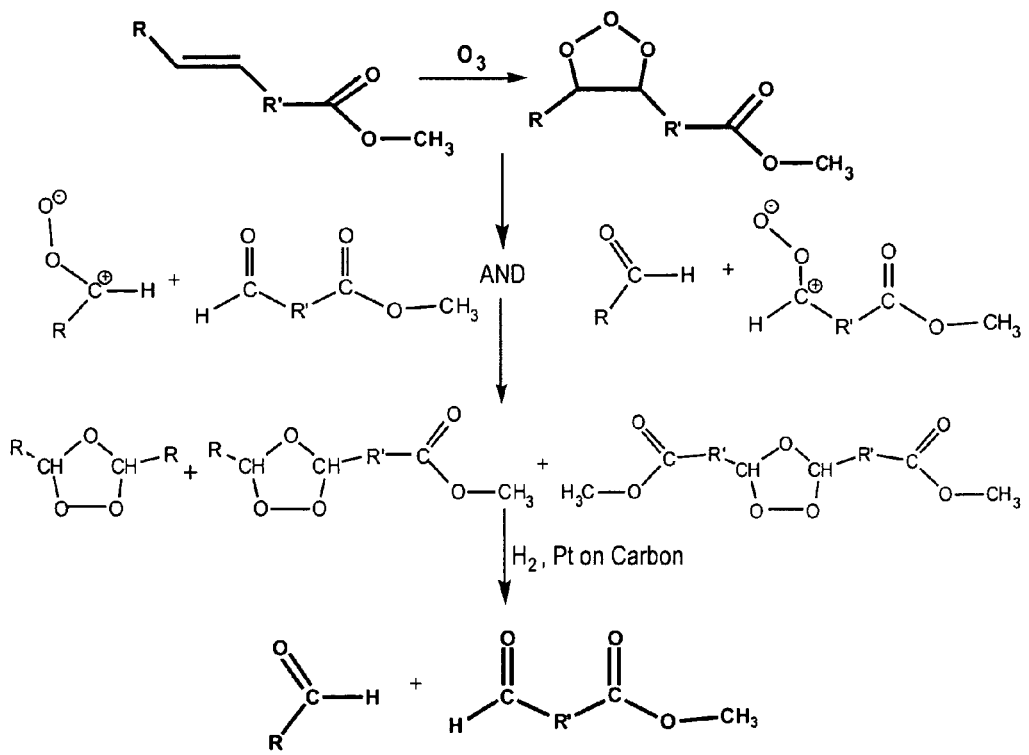

Because of its high oxidation potential ($E°=2.075$ V in acid and 1.246 V in base), ozone has been investigated as a powerful and environmentally benign oxidant in that it eventually decomposes to atmospheric oxygen. For example, ozonolysis of methyl oleate, $CH_3(CH_2)_7CH=CH(CH_2)_7C(=O)OCH_3$, followed by catalytic reduction in water gives yields of aldehydes approaching 90%. Detailed study of the meta-stable initial oxidation products has shown that 90% of the methyl oleate is transformed to 1,2,4-trioxolane, and 10% yield to peroxide oligomers (FIG. 1A). The latter should be accompanied by an equivalent molar amount of an aldehyde. The 1,2,4 trioxolane is formed by rearrangement of the initial product of 1,3 addition of ozone to the double bond, the 1,2,3-trioxolane. That rearrangement is understood to occur via a reversible dissociative process into an aldehyde and a zwitterionic peroxide. FIG. 1B shows the reaction scheme, which is expanded to display the complexity of intermediates that this dissociative process generates.

Figure 1C:
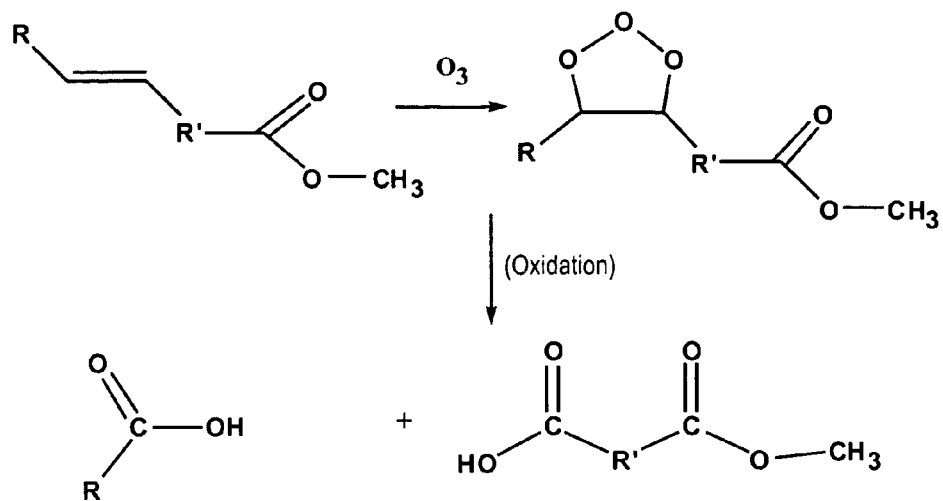

Despite the likelihood of seven or so intermediates (not counting geometric isomers), only a pair of products is formed, the aldehyde and the carboxy ester aldehyde. Significantly, if the ozonolysis reaction is followed by completion of the oxidation process, the products are a carboxylic acid and a dicarboxylic acid (FIG. 1C).

II. Ozonolysis

In one embodiment, the present invention provides improved processes and reaction conditions for performing ozonolysis with increased $O_3$ solubility in the liquid solvent (i.e., liquid medium). The processes and reaction conditions for performing ozonolysis can include the use of a liquid solvent that is substantially inert with respect to $O_3$ so as to limit the number and amount of unfavorable side products. The ozonolysis process can be performed where the $O_3$ solubility in the liquid phase is tunable with pressure so as to provide the ability to control reaction rate and product selectivity. Such processes and reactions can be achieved through the use of liquid $CO_2$ ($P_c$, $CO_2$=73.76 bar; $T_c$, $CO_2$=31.1° C. or 304.25 K) or $CO_2$-expanded liquids as the solvent medium.

In one embodiment, the ozonolysis can be performed with liquid $CO_2$ and various $CO_2$ expanded solvent liquids, such as natural unsaturated acids (e.g., oleic acid) or methyl esters thereof. The reaction rate for ozonolysis is most likely limited by the low solubility of ozone in the liquid phase. The use of $CO_2$ and $CO_2$-expanded liquids (CXLs) as reaction media can improve $O_3$ solubility as well as provide an inert environment for ozonolysis. In addition, non-flammable $CO_2$ is also miscible with low polarity solvents such as n-hexane. The ozonolysis followed by an appropriate hydrolytic, reductive or oxidative step can produce carboxylic acids, dicarboxylic acids, terminal carboxy alcohols or carboxy aldehydes. Significantly, similar results can be expected with other fatty acids having two or three carbon-carbon double bonds.

In one embodiment, ozonolysis can be performed in liquid $CO_2$. It is shown herein that $O_3$ is stable in liquid $CO_2$ and does not substantially react with $CO_2$. The solubility of $O_3$ in liquid $CO_2$ can be tuned continuously (e.g., increasing solubility up to about an order of magnitude) with relatively small changes in pressure around the critical pressure of ozone. For example, the solubility of $O_3$ in liquid $CO_2$ at $-0.7°$ C. (272.45 K) (e.g., 1.044 $T_c$, $O_3$) was experimentally determined to be approximately 0.006 absorbance unit at 52.4 bar (0.94 $P_c$, $O_3$) and 0.06 absorbance unit at 65.5 bar (1.18 $P_c$, $O_3$). Thus, the sensitive tunability of $O_3$ solubility in liquid $CO_2$ is related to the extreme compressibility of $O_3$ in the vicinity of its critical point.

$O_3$ is in the vicinity of its critical temperature (i.e., between 1 and 1.25 $T_c$, $O_3$) at $-0.7°$ C. (272.45 K). Hence, ozone compressibility (and therefore its density) will increase sharply as the pressure is isothermally increased beyond its critical pressure (e.g., above about 55.6 bar). On the other hand, air and $O_2$, which are the background gases in the $O_3$ stream at $-0.7°$ C. (272.45 K) are sufficiently far removed from their respective critical temperatures, and hence behave like ideal gases in the 50.6-66.9 bar pressure range, without displaying any sharp increase in compressibility. As such, even though the $O_3$ is present in dilute concentrations, such as on the order of a few mole percentage either in the air stream or in the $O_2$ stream, its compressibility, and therefore its density, increases sharply in the vicinity of its critical pressure, causing it to selectively dissolve in liquid $CO_2$. This phenomenon is akin to the increased dissolution of near-critical $CO_2$ in organic solvents as the pressure is increased beyond its critical pressure. Other advantages of increasing ozone concentration in $CO_2$ or $CO_2$-expanded liquids as the solvent medium are as follows: (i) reduced flammability hazards due to the presence of dense $CO_2$, which is a flame retardant, in the gas phase; (ii) $CO_2$ is less toxic than most organic solvents; (iii) use of $CO_2$ is considered environmentally benign if it is derived from existing, non-sequestered sources; and (iv) products can be easily separated from $CO_2$ solvent by pressure reduction.

The ozonolysis medium for the first step can be any liquid $CO_2$ at a variety of temperatures that are close to the critical temperature of ozone. The temperature of the ozone in liquid $CO_2$ can be between 0.75 and 1.5 $T_c$ of ozone, more preferably from about 0.9 to about 1.35 $T_c$ of ozone, and most preferably from about 0.95 to about 1.25 $T_c$ of ozone. Preferred temperatures of ozone in liquid $CO_2$ can be about 1, about 1.1, and about 1.15 $T_c$ of ozone. The temperature as a function of the $T_c$ is expressed in absolute units (Kelvin or Rankine); however, the temperature and temperature ranges can be converted to other units.

The ozonolysis medium for the first step can be any liquid $CO_2$ at a temperature close to the critical temperature of ozone and a suitable pressure close to the critical pressure. The pressure of the ozone in liquid $CO_2$ can be between 0.75 and 1.5 $P_c$ of ozone, more preferably from about 0.9 to about 1.35 $P_c$ of ozone, and most preferably from about 0.95 to about 1.25 $P_c$ of ozone. Preferred pressures of ozone in liquid $CO_2$ can be about 1, about 1.1, and about 1.15 $P_c$ of ozone. Stated differently, the pressure of the ozone in liquid $CO_2$ can be above about 40.5 bar, between about 45.6 bar and 76 bar, more preferably from about 50.7 bar to about 65.9 bar, and most preferably from about 54.7 bar to about 60.8 bar. Preferred pressures of ozone in liquid $CO_2$ can be about 52.7 bar, about 55.7 bar, and about 59.8 bar. The pressure as a function of Pc can be expressed in atmospheres (atm) or bar, and appropriate unit changes can be made for other pressure units.

The ozonolysis medium for the first step can be any liquid $CO_2$ having a variety of ozone densities that are close to and preferably above the critical density of ozone. The density of ozone can be between 0.75 and 1000 $\rho_c$, more preferably from about 0.9 to about 100 $\rho_c$, and most preferably from about 0.95 to about 10 $\rho_c$ of ozone.

The ozonolysis reaction is exothermic and the solvent can moderate the reaction rate, and therefore the rate of heat generation. Solvents, either inert or more inert compared to the substrate, act as a heat sink to absorb the heat of reaction. However, there are instances where a substrate can also be the solvent when provided in an amount sufficient to function as the solvent as well as provide sufficient substrate for the ozonolysis reaction.

Ozonolysis can be conducted in liquid solvents such as organic acids, alcohols, methylene chloride, ethyl acetate, THF, and even water; however, they can produce an array of intermediate peroxides. Water is desirable, but such reactions for higher molecular weight acids and esters can require the use of biphasic liquid systems. Alcohols are attractive because of good solubility relationships and in part because the solvent can reflect the alkyl group of the ester. The disadvantage of alcohols as solvents for ozonolysis is their susceptibility to oxidation, a factor that can present a hazard. In the present invention a solvent system such as a carbon dioxide expanded liquid (CXL), generated with low molecular weight alcohols, methanol and ethanol, can be used.

The effectiveness of the liquid solvents that are CXLs and other CXLs in catalytic oxidations can be increased using pure molecular oxygen. Their advantages include the high solubility of $O_2$ (e.g., as much as 100 fold over the organic solvent) and the safety benefit of a medium that is non-combustible and that will dominate the vapor phase in equilibrium with the reaction medium. In addition to process intensification based on increased oxidant solubility, molecular transport in CXLs is high compared to most media. Further, CXLs based on polar alcohols display that polarity in increased reaction rates compared to nonpolar media such as supercritical $CO_2$, or hydrocarbons.

Methanol-based CXLs can be used as a liquid medium for the oxidative cleavage of the methyl ester of oleic acid and those of higher unsaturated acids. Fatty acids such as palmitic acid exhibit limited solubility in either methanol or supercritical $CO_2$. The solubility of palmitic acid in supercritical $CO_2$ is on the order of $10^{-4}$ mole fraction even at pressures up to 150 bar. For example, soybean oil can also be used as a liquid medium for ozonolysis. The emulsion disappears and the methanol/soybean oil interface reappears when the $CO_2$ is released. This observation indicates the possibility of performing ozonolysis of fatty acid substrates dispersed as emulsion in $CO_2$-expanded methanol. Thus, carbon dioxide expanded methanol appears to be extremely well suited to ozone oxidation of the methyl esters of unsaturated acids to produce difunctional molecules of lower molecular weight and of significance as products of the bio-refinery. However, our results show that $O_3$ may attack methanol especially if the concentration of methanol is substantially higher than the substrate.

Some examples of solvents for a CXL that can be used for ozonolysis include: light hydrocarbon ($C_4$ or lower) liquids, methanol, ethanol, lower alcohols (e.g., $C_4$-$C_{10}$), higher alcohols (e.g., $C_{10}$-$C_{20}$) hexane, $SF_6$, xenon, water, aqueous solutions, fluorocarbon solvents, highly oxygenated molecules, highly fluorinated molecules, $CF_3CO_2H$, ionic liquids, strong liquid acids, $H_2SO_4$, $HSO_3F$, $HSO_3CF_3$, organic acids, saturated hydrocarbons, liquid substrates for ozonolysis, combinations thereof, and the like. The solubility of ozone in any of the aforementioned solvents can be increased by preparing a CXL as described herein.

In some instances, it can be preferable for the solvent in a CXL to be inert. Some examples of possible inert solvents for a CXL that can be used for ozonolysis can include: $SF_6$, xenon, water, aqueous solutions, fluorocarbon solvents, highly oxygenated molecules, highly fluorinated molecules, $CF_3CO_2H$, $H_2SO_4$, $HSO_3F$, and $HSO_3CF_3$.

Experiments have shown that some non-inert solvents may be used if the $O_3$ selectively attacks the substrate over the solvent (such is the case when using methanol as a solvent additive). That is, a liquid substrate can be used as a solvent in instances where the substrate desired to be reacted is more reactive with ozonolysis. This allows ozone to react more with the desired substrate rather then the solvent (e.g., possible substrate when used in inert or more inert solvents). For example, some substrate candidates, such as vegetable oils including soybean oil, which are known to be reactive with ozone can be used as solvents when the desired substrate is more reactive in comparison. In this context, the solvent is the more inert component of a solvent-substrate system. Thus, the solvent is the liquid that is either totally or substantially inert to ozone attack, or is less preferentially attacked by ozone in the presence of a more reactive substrate.

Some examples of possible non-inert solvents for a CXL that can be used for ozonolysis can include: methanol, ethanol, lower alcohols (e.g., $C_4$-$C_{10}$), higher alcohols (e.g., $C_{10}$-$C_{20}$) hexane, ionic liquids, liquid acids, organic acids, and saturated hydrocarbons.

Figure 2A:
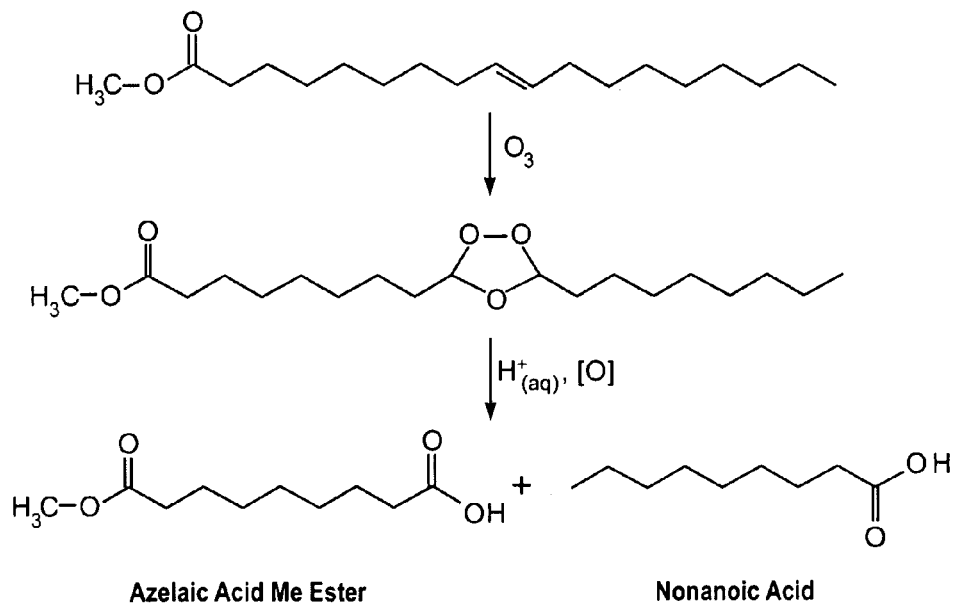
FIGS. 2A-2E are schematic representations of ozonolysis reactions.

In one embodiment, the ozonolysis process of the present invention can be used for oxidative cleavage of oils and fats, such as unsaturated fatty acids. The double bonds in unsaturated fatty acids provide reactive sites for performing a variety of transformations. Accordingly, oxidative scission of olefins can be obtained with ozonolysis. As shown in FIG. 2A, this highly selective reaction initially forms an ozonide, which can go on yield either aldehydes or carboxylic acids, with reductive or oxidative workup, respectively. This method is particularly attractive for producing carboxylic acids containing an odd number of carbon atoms in the polymethylene backbone. For example, industrially, azelaic acid is produced from oleic acid via ozonolysis, and is used in the manufacture of plasticizers, lubricants, hydraulic oils and cosmetics. It also is used as an anti-bacterial in acne treatments. Potential substrates for this ozonolysis reaction are extensive, and include fatty acids, their esters, and other sources of oil and fats.

Figure 2B:
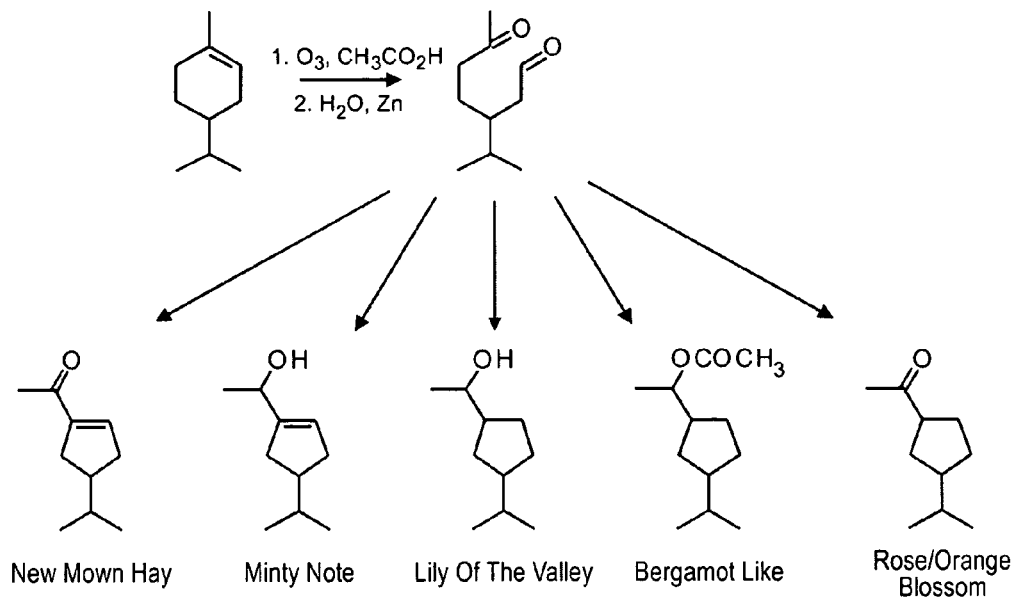

In one embodiment, the ozonolysis process can be used for preparing ingredients and reagents for perfume and fragrance chemistry. For example, ozonation of terpenes can be used to preparing ingredients and reagents. Oxygenated compounds form the bulk of most odiferous chemistry, so it is not surprising that the ozonolytic fission of alkenes is used extensively in the perfume and fragrance industries. There is an extensive chemistry associated with the production of various fragrant molecules from the terpenes, and the majority of synthetic routes begin with the ozonolytic cleavage of an allylic moiety within the terpene molecule. For example, ozonolysis of the terpene, (+)-p-menth-1-ene can form, by reductive workup, (−)-3-isopropyl-6-oxoheptanal. This molecule can then undergo a variety of reactions to form several fragrant molecules (e.g., new mown hay, minty note, lily of the valley, bergamot-like, rose/orange blossom, and the like) as shown in FIG. 2B.

Figure 2C:
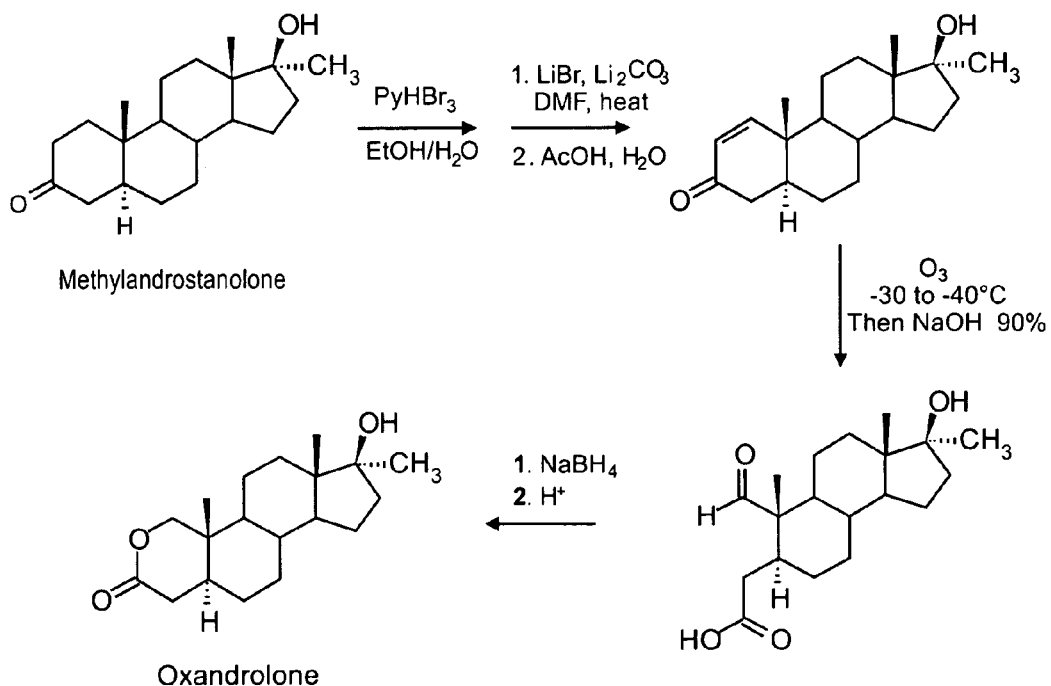

In one embodiment, the ozonolysis process can be used for preparing active agents for pharmaceutical products or reagents for making pharmaceutical products. Ozonolysis of suitable substrates, such as natural products or bioactive agents, can be used to prepare new bioactive agents or derivatives of various biological active molecules. For example, oxandrolone is an anabolic steroid used to promote weight gain in patients who have experienced surgery, chronic infection or severe trauma. It also relieves bone pain associated with osteoporosis. It was originally developed by G.D. Searle Company and was synthesized from methylandrostanolone via a multistep route involving the use of highly toxic $OsO_4$ and $Pb(OAc)_4$. An alternative route for multi kilogram quantities of USP Oxandrolone has been developed by Cedarburg Pharmaceuticals, Inc., which utilizes an ozonolysis reaction to produce a key intermediate acid in good yields while avoiding the use of highly toxic, persistent reagents and the associated problems with the accumulation of hazardous waste. As shown in FIG. 2C, the ozonolysis process of the present invention can be used to prepare oxandrolone in a safer, more economical process.

Figure 2D:
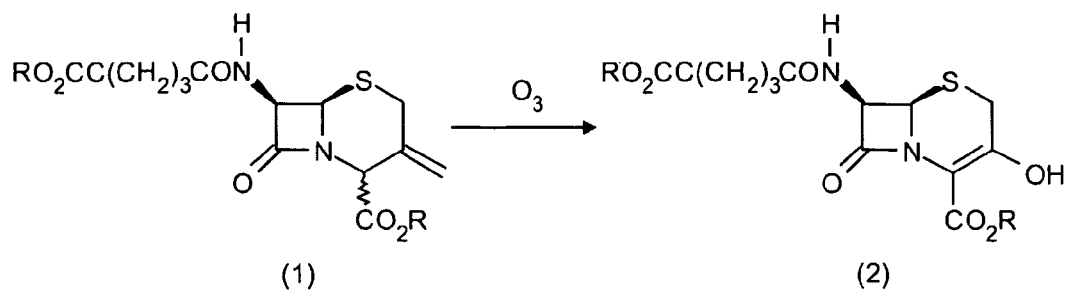

In another example, the ozonolysis process of the present invention can be used to prepare antibiotics, such as cefaclor and ceftibuten, from suitable substrates. Cefaclor and ceftibuten are compounds belonging to a class of medications called cephalosporin antibiotics. They are effective against a wide range of infections and were discovered by Shionogi and Co. Ltd., Osaka, Japan. Originally they were produced synthetically from penicillin sulfoxides, but attempts to reduce the cost of production by scientists at the Schering Plough Research Institute have resulted in synthetic routes from cephalosporin C broths. A key step in this route is an ozonolysis step which converts the 3-exomethylene cephalosporin (1) into 3-hydroxycephem (2). As shown in FIG. 2D, the ozonolysis process of the present invention can be used to prepare 3-hydroxycephem (2) in a safer, more economical process.

Figure 2E:
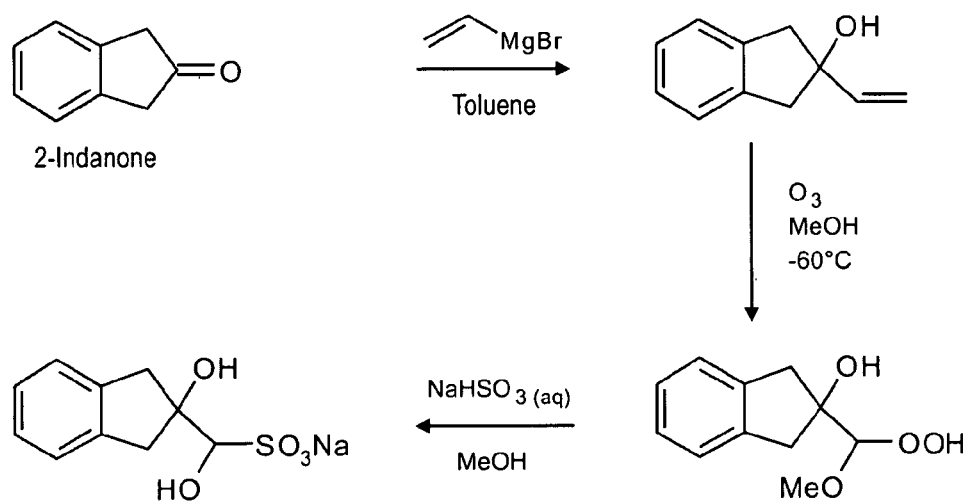

In another example, the ozonolysis process of the present invention can be used to prepare 2-Hydroxyindan-2-carboxaldehyde. Pfizer previously developed a multi-kilogram scale synthesis for the 2-indanone derived aldehyde, 2-hydroxyindan-2-carboxaldehyde, which is used in a reductive amination reaction. 2-Indanone undergoes a Grignard addition with vinylmagnesium bromide to yield a tertiary allylic alcohol. This undergoes ozonolysis in methanol, and subsequently the solvent traps the carbonyl oxide intermediate to form the methoxy-hydroperoxide. The hydroperoxide is the reduced with sodium bisulfite to form a stable bisulfite adduct which is used in the reductive amination in preference to the aldehyde. As shown in FIG. 2E, the ozonolysis process of the present invention can be used to prepare 2-hydroxyindan-2-carboxaldehyde in a safer, more economical process.

In one embodiment, the ozonolysis process of the present invention can be useful for non-olefin oxidation reactions. For example, the non-olefin oxidation reactions can be the oxidation of benzylic substrates and the like via ozonolysis. Accordingly, the chemistry of ozonolysis of organics substrates is not limited to the selective cleavage of double bonds. It has been shown that ozone can efficiently oxidize substituted benzylic compounds to their corresponding benzaldehydes and benzoic acids using a transition metal catalyst. As such, solvent and reaction conditions described herein and using manganese(II) acetate as the catalyst, the oxidation of toluene derivatives can be directed to either the aldehyde or the carboxylic acid products. The only off-gas produced is oxygen. The ozonolysis process of the present invention can be used to prepare benzaldehydes and benzoic acids in a safer, more economical process.

In one embodiment, the ozonolysis process of the present invention can be used for the production of singlet oxygen. The production of singlet oxygen from ozone has received some attention recently. Conventional methods for production involve irradiating oxygen gas with ultraviolet light in the presence of a sensitizer, such as tetraphenylporphyrin. The presence of large quantities of dioxygen, organic solvents and light, in addition to the costs of special gas/liquid photoreactors, have discouraged industrial application and limited the industrial use to small scale applications in flavor and perfume production. Consequently, dark methods of producing $^1O_2$ have been extensively investigated, with the catalytic conversion of hydrogen peroxide by molybdate being the most attractive. Ozone can also be used to produce $^1O_2$ and it has been shown that 1,1'-bis(diphenylphosphino)ferrocene promotes splitting of ozone to give $^1O_2$. Accordingly, the ozone in $CO_2$ or CXL along with 1,1'-bis(diphenylphosphino)ferrocene can be used to produce $^1O_2$. Also, by reductive recycling of (e.g., hydrogenating) the oxidized form of the ferrocene catalyst, a continuous process can be conducted to produce $^1O_2$.

In one embodiment, the ozonolysis process of the present invention can be used for the oxidation of methane. The enhanced ozone solubility in $CO_2$ or CXL can be used for the oxidation of methane via ozonolysis. Previously, oxidation of methane has been reported to transform methane to protonated formaldehyde in super acid media. In such powerful acid solutions, methane has also been reported to be oxidized, along with oligomerization, to protonated acetone or to the related alkyl carbenium ion. Now, such transformations can be performed with ozone in $CO_2$ or CXL.

The ozonolysis process of the present invention can be applied to a wide variety of substrates. The most common substrates can be vegetable fatty acids, esters of fatty acids, fats and oils. Examples of vegetable fatty acids are selected from the group consisting of butyric acid, caproic acid, caprylic acid, capric acid, lauric acid, myristic acid, palmitic acid, stearic acid, arachic acid, behenic acid, lignoceric acid, hexacosanoic acid, octacosanoic acid, triacontanoic acid and n-dotriacontanoic acid, and those having an odd number of carbon atoms, such as propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid, heptacosanoic acid, isobutyric acid, isocaproic acid, isocaprylic acid, isocapric acid, isolauric acid, 11-methyldodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, α-ethyl-hexanoic acid, α-hexyldecanoic acid, α-heptylundecanoic acid, 2-decyltetradecanoic acid, 2-undecyltetradecanoic acid, 2-decylpentadecanoic acid, 2-undecylpentadecanoic acid, Fine oxocol 1800 acid (product of Nissan Chemical Industries, Ltd.), 6-methyl-octanoic acid, 8-methyl-decanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic, 26-methyloctacosanoic acid, including 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid (18:3 n3), gamma linolenic acid (18:3 n6), α-eleostearic acid, gadoleic acid (20:1), α-eleostearic acid, punicic acid, 6,9,12,15-octadecatetraenoic acid, parinaric acid, 5,8,11,14-eicosatetraenoic acid, erucic acid, 5,8,11,14,17-eicosapentaenoic acid (EPA), 7,10,13,16,19-docosapentaenoic acid, 4,7,10,13,16,19-docosahexaenoic acid (DHA), α-hydroxylauric acid, α-hydroxymyristic acid, α-hydroxypalmitic acid, α-hydroxystearic acid, ω-hydroxylauric acid, α-hydroxyarachic acid, 9-hydroxy-12-octadecenoic acid, ricinoleic acid, α-hydroxybehenic acid, 9-hydroxy-trans-10,12-octadecadienic acid, kamolenic acid, ipurolic acid, 9,10-dihydroxystearic acid, 12-hydroxystearic acid, oxalic acid, citric acid, malonic acid, succinic acid, glutaric acid, adipic acid, pimelic acid, suberic acid, azelaic acid, sebacic acid, D,L-malic acid, derivatives of any thereof, and combinations of any thereof.

Examples of esters of fatty acids are selected from the group consisting of methyl laurate, methyl myristate, methyl palmitate, methyl oleate, methyl elaidate, methyl linoleate, methyl linolenate, methyl stearate, methyl erucate, methyl ricinoleate, methyl licanate, methyl elaeostearate, methyl arachidonate, methyl clupanodonate, ethyl laurate, ethyl myristate, ethyl palmitate, ethyl oleate, ethyl elaidate, ethyl linoleate, ethyl linolenate, ethyl stearate, ethyl erucate, ethyl ricinoleate, ethyl lincanate, ethyl elaeostearate, ethyl arachidonate, ethyl clupanodonate, propyl laurate, propyl myristate, propyl palmitate, propyl oleate, propyl elaidate, propyl linoleate, propyl linolenate, propyl stearate, propyl erucate, propyl ricinoleate, propyl licanate, propyl elaeostearate, propyl arachidonate, propyl clupanodonate, isopropyl laurate, isopropyl myristate, isopropyl palmitate, isopropyl oleate, isopropyl elaidate, isopropyl linoleate, isopropyl linolenate, isopropyl stearate, isopropyl erucate, isopropyl ricinoleate, isopropyl licanate, isopropyl elaeostearate, isopropyl arachidonate, isopropyl clupanodonate, butyl laurate, butyl myristate, butyl palmitate, butyl oleate, butyl elaidate, butyl linoleate, butyl linolenate, butyl stearate, butyl erucate, butyl ricinoleate, butyl licanate, butyl elaeostearate, butyl arachidonate, butyl clupanodonate, sec.butyl laurate, sec.butyl myristate, sec.butyl palmitate, sec. butyl oleate, sec.butyl elaidate, sec.butyl linoleate, sec.butyl linolenate, sec.butyl stearate, sec.butyl erucate, sec.butyl ricinoleate, sec.butyl licanate, sec.butyl elaeostearate, sec.butyl arachidonate, sec.butyl clupanodonate, isobutyl laurate, isobutyl myristate, isobutyl palmitate, isobutyl oleate, isobutyl elaidate, isobutyl linoleate, isobutyl linolenate, isobutyl stearate, isobutyl erucate, isobutyl ricinoleate, isobutyl licanate, isobutyl elaeostearate, isopropyl arachidonate, isobutyl clupanodonate, amyl laurate, amyl myristate, amyl palmitate, amyl oleate, amyl elaidate, amyl linoleate, amyl linolenate, amyl stearate, amyl erucate, amyl ricinoleate, amyl licanate, amyl elaeostearate, amyl arachidonate, amyl clupanodonate, hexyl laurate, hexyl myristate, hexyl palmitate, hexyl oleate, hexyl elaidate, hexyl linoleate, hexyl linolenate, hexyl stearate, hexyl erucate, hexyl ricinoleate, hexyl licanate, hexyl elaeostearate, hexyl arachidonate, hexyl clupanodonate, heptyl laurate, heptyl myristate, heptyl palmitate, heptyl oleate, heptyl elaidate, heptyl linoleate, heptyl linolenate, heptyl stearate, heptyl erucate, heptyl ricinoleate, heptyl lincanate, heptyl elaeostearate, heptyl arachidonate, heptyl clupanodonate, octyl laurate, octyl myristate, octyl palmitate, octyl oleate, octyl elaidate, octyl linoleate, octyl linolenate, octyl stearate, octyl erucate, octyl ricinoleate, octyl licanate, octyl elaeostearate, octyl arachidonate, octyl clupanodonate, 2-ethylhexyl laurate, 2-ethylhexyl myristate, 2-ethylhexyl palmitate, 2-ethylhexyl oleate, 2-ethylhexyl elaidate, 2-ethylhexyl linoleate, 2-ethylhexyl linolenate, 2-ethylhexyl stearate, 2-ethylhexyl erucate, 2-ethylhexyl ricinoleate, 2-ethylhexyl licanate, 2-ethylhexyl elaeostearate, 2-ethylhexyl arachidonate, 2-ethylhexyl clupanodonate, t-butyl laurate, t-butyl myristate, t-butyl palmitate, t-butyl oleate, t-butyl elaidate, t-butyl linoleate, t-butyl linolenate, t-butyl stearate, t-butyl erucate, t-butyl ricinoleate, t-butyl licanate, t-butyl elaeostearate, t-butyl arachidonate, t-butyl clupanodonate, isooctyl laurate, isooctyl myristate, isooctyl palmitate, isooctyl oleate, isooctyl elaidate, isooctyl linoleate, isooctyl linolenate, isooctyl stearate, isooctyl erucate, isooctyl ricinoleate, isooctyl licanate, isooctyl elaeostearate, isooctyl arachidonate, isooctyl clupanodonate, nonyl laurate, nonyl myristate, nonyl palmitate, nonyl oleate, nonyl elaidate, nonyl linoleate, nonyl linolenate, nonyl stearate, nonyl erucate, nonyl ricinoleate, nonyl licanate, nonyl elaeostearate, nonyl arachidonate, nonyl clupanodonate, decyl laurate, decyl myristate, decyl palmitate, decyl oleate, decyl elaidate, decyl linoleate, decyl linolenate, decyl stearate, decyl erucate, decyl ricinoleate, decyl licanate, decyl elaeostearate, decyl arachidonate, decyl clupanodonate, undecyl laurate, undecyl myristate, undecyl palmitate, undecyl oleate, undecyl elaidate, undecyl linoleate, undecyl linolenate, undecyl stearate, undecyl erucate, undecyl ricinoleate, undecyl licanate, undecyl elaeostearate, undecyl arachidonate, undecyl clupanodonate, dodecyl laurate, dodecyl myristate, dodecyl palmitate, dodecyl oleate, dodecyl elaidate, dodecyl linoleate, dodecyl linolenate, dodecyl stearate, dodecyl erucate, dodecyl ricinoleate, dodecyl licanate, dodecyl elaeostearate, dodecyl arachidonate, dodecyl clupanodonate, methyl brasidate, ethyl brasidate, propyl brasidate, isopropyl brasidate, butyl brasidate, sec-butyl braisidate, isobutyl brasidate, t-butyl brasidate, amyl brasidate, hexyl brasidate, heptyl brasidate, octyl brasidate, 2-ethylhexyl brasidate, isooctyl brasidate, nonyl brasidate, decyl brasidate, undecyl brasidate, dodecyl brasidate, hydroxyethyl laurate, hydroxyethyl myristate, hydroxyethylpalmitate, hydroxyethyl oleate, hydroxyethyl elaidate, hydroxyethyl linoleate, hydroxyethyl linolenate, hydroxyethyl stearate, hydroxyethyl erucate, hydroxyethyl ricinoleate, hydroxyethyl licanate, hydroxyethyl elaeostearate, hydroxyethyl arachidonate, hydroxyethyl clupanodonate, hydroxyethyl brasidate, polyethoxylated lauric acid, polyethoxylated myristic acid, polyethoxylated palmitic acid, polyethoxylated oleic acid, polyethoxylated elaidic acid, polyethoxylated linoleic acid, polyethoxylated linolenic acid, polyethoxylated stearic acid, polyethoxylated erucic acid, polyethoxylated ricinoleic acid, polyethoxylated licanic acid, polyethoxylated elaeostearic acid, polyethoxylated arachidonic acid, polyethoxylated clupanodonic acid, polyethoxylated brasidic acid, hydroxpropyl laurate, hydroxypropyl myristate, hydroxypropyl palmitate, hydroxypropyl oleate, hydroxypropyl elaidate, hydroxypropyl linoleate, hydroxypropyl linolenate, hydroxypropyl stearate, hydroxypropyl erucate, hydroxypropyl ricinoleate, hydroxypropyl licanate, hydroxypropyl elaeostearate, hydroxypropyl arachidonate, hydroxypropyl clupanodonate, hydroxypropyl brasidate, polypropoxylated lauric acid, polypropoxylated myristic acid, polypropoxylated palmitic acid, polypropoxylated oleic acid, polypropoxylated elaidic acid, polypropoxylated linoleic acid, polypropoxylated linolenic acid, polypropoxylated stearic acid, polypropoxylated erucic acid, polypropoxylated ricinoleic acid, polypropoxylated licanic acid, polypropoxylated elaeostearic acid, polypropoxylated arachidonic acid, polypropoxylated clupanodonic acid, polypropoxylated brasidic acid, cyclopentyl laurate, cyclopentyl myristate, cyclopentyl palmitate, cyclopentyl oleate, cyclopentyl elaidate, cyclopentyl linoleate, cyclopentyl linolenate, cyclopentyl stearate, cyclopentyl erucate, cyclopentyl ricinoleate, cyclopentyl licanate, cyclopentyl elaeostearate, cyclopentyl arachidonate, cyclopentyl clupanodonate, cyclopentyl brasidate, cyclohexyl laurate, cyclohexyl myristate, cyclohexyl palmitate, cyclohexyl oleate, cyclohexyl elaidate, cyclohexyl linoleate, cyclohexyl linolenate, cyclohexyl stearate, cyclohexyl erucate, cyclohexyl ricinoleate, cyclohexyl licanate, cyclohexyl elaeostearate, cyclohexyl arachidonate, cyclohexyl clupanodonate, cyclohexyl brasidate, methoxyethyl laurate, methoxyethyl myristate, methoxyethyl palmitate, methoxyethyl oleate, methoxyethyl elaidate, methoxyethyl linoleate, methoxyethyl linolenate, methoxyethyl stearate, methoxyethyl erucate, methoxyethyl ricinoleate, methoxyethyl licanate, methoxyethyl elaeostearate, methoxyethyl arachidonate, methoxyethyl clupanodonate, methoxyethyl brasidate, isopropoxyethyl laurate, isopropoxyethyl myristate, isopropoxyethyl palmitate, isopropoxyethyl oleate, isopropoxyethyl elaidate, isopropoxyethyl linoleate, isopropoxyethyl linolenate, isopropoxyethyl stearate, isopropoxyethyl ercuate, isopropoxyethyl ricinoleate, isopropoxyethyl licanate, isopropoxyethyl elaeostearate, isopropoxyethyl arachidonate, isopropoxyethyl clupanodonate, isopropoxyethyl brasidate, butoxyethyl laurate, butoxyethyl myristate, butoxyethyl palmitate, butoxyethyl oleate, butoxyethyl elaidate, butoxyethyl linoleate, butoxyethyl linolenate, butoxyethyl stearate, butoxyethyl erucate, butoxyethyl elaeostearate, butoxyethyl licanate, butoxyethyl ricinoleate, butoxyethyl arachidonate, butoxyethyl clupanodonate, butoxyethyl brasidate, methoxypropyl laurate, methoxypropyl myristate, methoxypropyl palmitate, methoxypropyl oleate, methoxypropyl elaidate, methoxypropyl linoleate, methoxypropyl linolenate, methoxypropyl stearate, methoxypropyl erucate, methoxypropyl ricinoleate, methoxypropyl licanate, methoxypropyl elaeostearate, methoxypropyl arachidonate, methoxypropyl clupanodonate, methoxypropyl brasidate, ethoxypropyl laurate, ethoxypropyl myristate, ethoxypropyl palmitate, ethoxypropyl oleate, ethoxypropyl elaidate, ethoxypropyl linoleate, ethoxypropyl linolenate, ethoxypropyl stearate, ethoxypropyl erucate, ethoxypropyl ricinoleate, ethoxypropyl licanate, ethoxypropyl elaeostearate, ethoxypropyl arachidonate, ethoxypropyl clupanodonate, ethoxypropyl brasidate, butoxypropyl laurate, butoxypropyl myristate, butoxypropyl palmitate, butoxypropyl oleate, butoxypropyl elaidate, butoxypropyl linoleate, butoxypropyl linolenate, butoxypropyl stearate, butoxypropyl erucate, butoxypropyl ricinoleate, butoxypropyl licanate, butoxypropyl elaeostearate, butoxypropyl arachidonate, butoxypropyl clupanodonate, butoxypropyl brasidate, isopropoxypropyl laurate, isopropoxypropyl myristate, isopropoxypropyl palmitate, isopropoxypropyl oleate, isopropoxypropyl telaidate, isopropoxypropyl linoleate, isopropoxypropyl linolenate, isopropoxypropyl stearate, isopropoxypropyl erucate, isopropoxypropyl ricinoleate, isopropoxypropyl licanate, isopropoxypropyl elaeostearate, isopropoxypropyl arachidonate, isopropoxypropyl clupanodonate, isopropoxypropyl brasidate, and the like.

Examples of fats and oils are selected from the group consisting of animal fat, beef tallow, borneo tallow, butterfat, camelina oil, candlefish oil, canola oil, castor oil, cocoa butter, cocoa butter substitutes, coconut oil, cod-liver oil, coriander oil, corn oil, cottonseed oil, flax oil, hazelnut oil, hempseed oil, herring oil, illipe fat, jatropha oil, kokum butter, lanolin, lard, linseed oil, mango kernel oil, marine oils, meadowfoam oil, menhaden oil, milk fat, mowrah fat, mustard oil, mutton tallow, neat's foot oil, olive oil, orange roughy oil, palm oil, palm kernel oil, palm kernel olein, palm kernel stearin, palm olein, palm stearin, peanut oil, phulwara butter, pile herd oil, rapeseed oil, rice bran oil, safflower oil, sal fat, sardine oil, sasanqua oil, shea fat, shea butter, soybean oil, sunflower seed oil, tall oil, tallow, tsubaki oil, tung oil, vegetable oil, whale oil, triacylglycerols, diacylglycerols, monoacylglycerols, triolein, triglycerides of medium chain fatty acids, and derivatives, conjugated derivatives, genetically-modified derivatives and mixtures thereof. Other sources of suitable fatty acids include used cooking oils, float grease from wastewater treatment plants, animal fats such as beef tallow and pork lard, crude oils, "yellow grease," i.e., animal or vegetable oils and fats that have been used or generated as a result of the preparation of food by a restaurant or other food establishment that prepares or cooks food for human consumption with a free fatty acid content of less than 15%, and white grease, i.e., rendered fat derived primarily from pork, and/or other animal fats.

In one embodiment, the substrate for ozonolysis can be soluble or substantially soluble or suspendable in liquid $CO_2$. Some examples can include propylene, 1-butene, cyclopentene, cyclohexene, cycloheptene, cyclooctene, cis-stilbene, trans-stilbene, and similar types of compounds.

However, some of the substrates that may be desired to be reacted through ozonolysis may not be soluble in either carbon dioxide or carbon dioxide-expanded liquids. Such immiscible liquid phases are not uncommon in industrial processes. In such cases, the interfacial surface area can be increased to overcome the mass transfer limitations, and thereby enhance the reaction rate. The interfacial surface area can be increased by intense agitation either with a mechanical stirrer or an ultrasonic mixing device, either of which creates an emulsion or dispersion of the substrate in the solvent phase. Other means for intense agitation can also be used to increase the interfacial surface. Thus, the present invention can be used in reactions where the substrate is not completely soluble in the solvent. This is particularly true of important substrates from biomass including many components of bio-oils of the many kinds described herein.

III. Catalysis

As shown in FIGS. 1A and 1B, the reaction with the substrate to obtain a desired product may occur in two steps. The first step is ozonolysis in $CO_2$ or $CO_2$ expanded liquids (i.e., CXL), as described herein. The second step in the overall process may be catalytic or stoichiometric depending on the specific case under development. For example, it is reported that hydrolysis of the trioxolane will produce the corresponding dicarboxylic acids, and that hydrolysis in the presence of a mild reductant will produce the aldehydes. Examination of the balanced equations reveals that simple use of the states of oxidation in the trioxolane will produce one mole of ketone/aldehyde and one mole of carboxylic acid. In fact, gentle reduction during cleavage of the trioxolane will convert both emerging moieties to aldehydes while oxidative cleavage will produce two moles of carboxylic acid. Strong reduction will yield two moles of alcohol. Thus, new catalytic processes can be used for the second step in ozonolysis or ozone-based conversion of unsaturated acids and their esters into useful, lower molecular weight products.

In one embodiment, the first and/or second step of the ozonolysis process can be performed with a catalytic system. Known catalytic systems are not effective at accelerating the use of the full oxidizing power of ozone in reactions in general and in the cleavage of carbon-carbon double bonds in particular. Catalysis of the initial oxidation process by a transition metal catalyst can moderate the oxidative power of the ozone. Catalysts generally moderate ozone in two ways; by elimination of the mechanistic pathways available to the ozone molecule, and, because of the apparent conversion of ozone into hydroxyl radical plus less reactive products, the selectivity of the oxidant is lost and the yields of desired products are diminished. In the absence of catalysts, ozone converts carbon-carbon double bond groups into meta-stable intermediates, 1,2,4-trioxolanes, that are well-suited to efficient second steps (solvolysis, oxidation, reduction) that may lead to a readily selected array of desirable products. However, the desirability of catalysis in the second step, the transformation of the 1,2,4-ozonide to desirable products, can be improved by catalysis, whether it be oxidation or reduction. Accordingly, catalysts can be used with the ozonolysis of substrates in $CO_2$ and CXLs as described herein. Examples of some catalysis can include, with a view toward using transition metal ions as catalysts, iron(III) oxide, iron, cobalt, nickel, copper, manganese, chromium, manganese (e.g., Mn(III) not Mn(VII)), osmium, ruthenium and rhenium, manganese porphyrins, manganese centered polyoxometallates, titanium, $TiO_2$, combinations thereof, oxides thereof, and the like.

IV. Ozone Purification

Additionally, the present invention provides process and reaction conditions for preparing ozone or increasing ozone purity. Ozone can be present in a gas, such as air or oxygen, or can be separated therefrom. Ozone generation is well known in the art. The ozone is often accompanied by the gas from which it was generated. Now, the ozone can be selectively purified from the original gas.

In one embodiment, the ozone can be separated from oxygen or air in the presence of $CO_2$ or CXL by increasing the pressure of the system at a temperature close to the $T_c$ of ozone. That is, the same conditions for increasing ozone concentration in $CO_2$ or CXL can be used for purifying ozone from the gas. As such, the $CO_2$ or CXL compositions in the presence of ozone can be modulated by increasing pressure at a temperature close to the Tc without a substrate. The lack of a substrate allows the $O_3$ to be separated from either an $O_2+O_3$ or an $O_3$+air stream by being concentrated in the $CO_2$ or CXL without reacting and degrading the ozone. The separation process can be performed by cooling the $O_2$/air+$O_3$ mixtures just below the critical temperature of $O_3$ (e.g., −12° C. or 261.15 K) in order to condense out the $O_3$ by simply increasing the system pressure (e.g., a few tens of bars close to the critical pressure of $O_3$). This method can be cheaper and easier than refrigeration techniques to separate $O_3$.

After the concentration of ozone is increased in $CO_2$ or CXL, all of the gas not in the liquid can be removed. The ozone gas in the liquid can then be separated from the liquid so as to obtain purified ozone.

Experimental

1.

Figure 3:
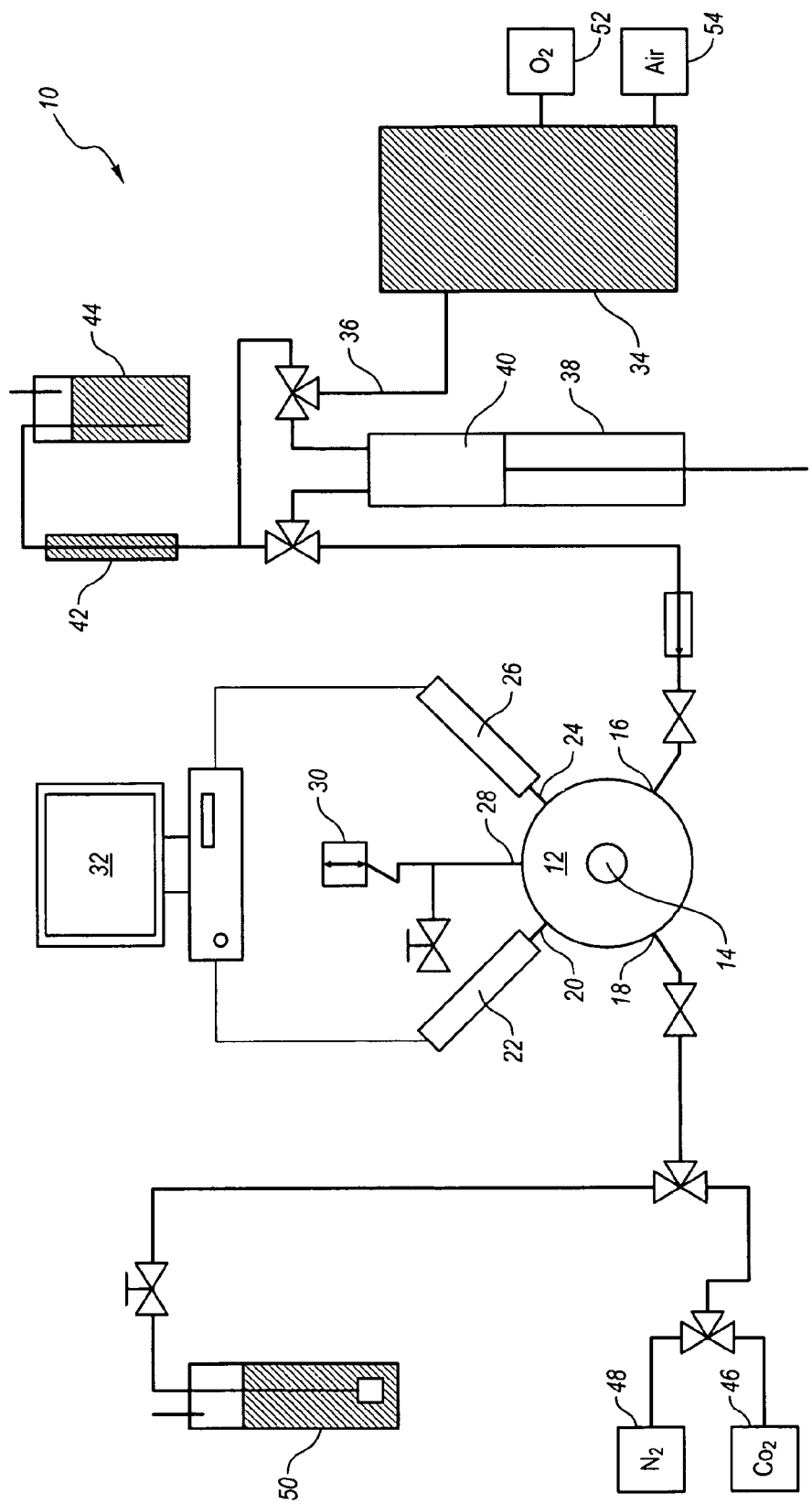
FIG. 3 is a schematic diagram of a system for performing ozonolysis or purifying ozone from a gas.

The ozone concentration measurements and the ozonolysis experiments were performed using a 10 $cm^3$ titanium high pressure view cell. A schematic representation of the reactor system 10 is shown in FIG. 3. The reactor system 10 is shown to include a high pressure reaction cell 12 that is cylindrical in shape, but can be in any other shape. The cell 12 is fitted with view window 14, such as sapphire windows at both ends, which are sealed with PEEK O-rings and screw caps (not shown). A spectrophotometer (not shown) (e.g., Ocean Optics fiber optic UV/Visible spectrophotometer) is used to measure UV/Visible spectra via the sapphire windows 14. The body of the cell 12 is fitted with a port for ozone input 16, a port for $CO_2$ and/or CXL input 18, a port for a thermocouple 22 input 20, a port for a pressure transducer 26 input 24, and a port 28 for a safety rupture disk 30. The ozone input 16 can be fitted with a titanium frit (not shown) to ensure good mixing of the ozone with the contents of the cell 12. Samples can be withdrawn from either the liquid or gas phase via any of the ports. Mixing is performed using a magnetic stirrer bar (not shown) and temperature adjustments made using a circulating fluid thermal jacket (not shown) in contact with the cell 12. Temperature was monitored with the thermocouple 22, and controlled and recorded using a computer controlled data acquisition system 32 (Dasylab, measX GmbH & Co.KG). Pressure was monitored with the pressure transducer 26, and controlled and recorded using the computer controlled data acquisition system 32.

Ozone is generated by an ozone generator 34 (e.g., Praxair-Trailgaz Unizone™ Lo corona discharge ozone generator) from either a compressed air or oxygen source. The ozone containing gas stream 36 is then led to a pump 38 (e.g., Teledyne ISCO 500D syringe pump) where the ozone-containing stream fills the feed reservoir 40. The reservoir 40 contents are compressed to a pressure suitable for introduction into the reaction cell 12. Excess ozone is destroyed by passing the exiting gas stream over a magnesium oxide catalyst packed tube 42 followed by bubbling through an aqueous sodium hydroxide solution 44. The bottom left input port 18 is used to introduce carbon dioxide from a carbon dioxide source 46 and/or nitrogen from a nitrogen source 48 into the reaction cell 12, and also to remove products at the end of a reaction cycle. Products are collected by bubbling the product stream through a chilled solvent 50. The top port 28 houses a rupture disk 30 and can also be used for product collection.

2.

To guide the experiments in $CO_2$-expanded solvents, the miscibility and volumetric expansion of the following mixtures in dense $CO_2$ can be determined in a Jurgeson® view cell at typical operating temperatures (10-25° C. or 282.15-298.15 K). Description of the Jurgeson® view cell and the experimental procedure for measuring the volumetric expansion are given elsewhere (Ghezai Musie, Ming Wei, Bala Subramaniam, and Daryle H. Busch, "Catalytic Oxidations in Carbon Dioxide-based Reaction Media, including novel $CO_2$-expanded phases," *Coord. Chem. Revs.*, 219-221, 789-820 (2001); Ming Wei, Ghezai T. Musie, Daryle H. Busch and Bala Subramaniam, "$CO_2$-expanded Solvents: Unique and Versatile Media for Performing Homogeneous Catalytic Oxidations," *J. Am. Chem. Soc.*, 124, 2513-17 (2002)).

3.

Experiments were performed to determine liquid-phase $O_3$ concentrations. In a typical experiment to determine ozone concentration in liquid $CO_2$, a quantity of $CO_2$ is introduced into the cell (maintained at a desired temperature) via one of the ports to a pressure at which $CO_2$ forms a liquid phase and the cell pressure noted. The liquid level in the cell reaches above the windows allowing a complete path for a UV/Visible light spectrum through the liquid phase. The gas output ($O_2$/$O_3$ mixture) from the ozone generator is compressed using the ISCO syringe pump to a pressure above the cell pressure. The ozone containing mixture is then allowed to enter the cell through an inlet port and allowed to equilibrate before a UV/Visible spectrum of the liquid phase $CO_2$ is measured. More ozone is added repeatedly and a UV/Visible spectrum measured after each addition, following equilibration, until the maximum desired pressure is reached.

Figure 4A:
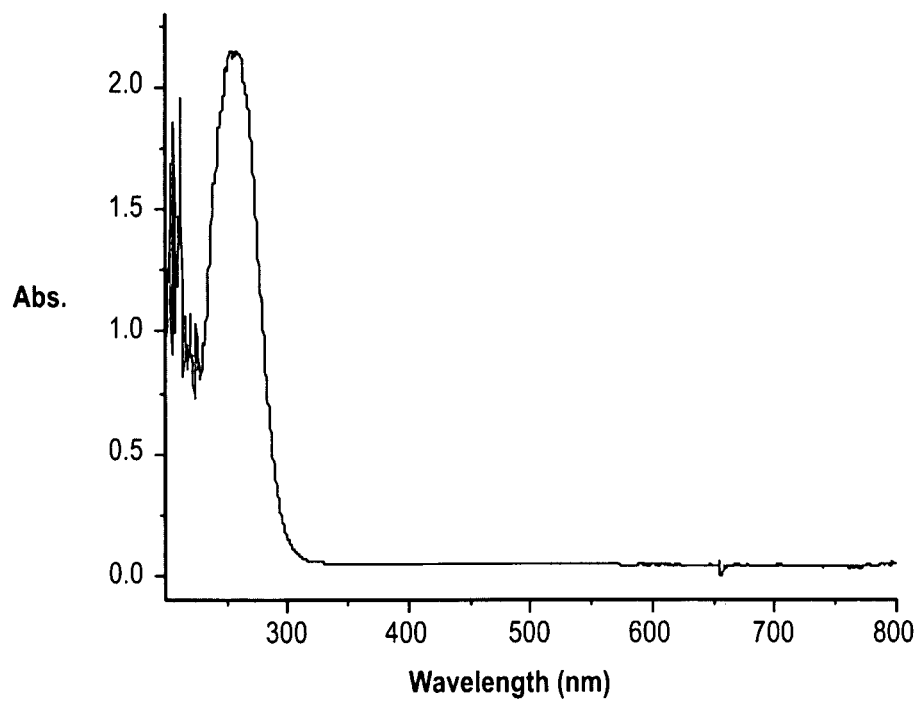
FIGS. 4A-4B are graphs showing the UV/Visible spectrum of ozone, which has the strong absorption Hartley Band and the weak absoption Chappuis Band.
Figure 4B:
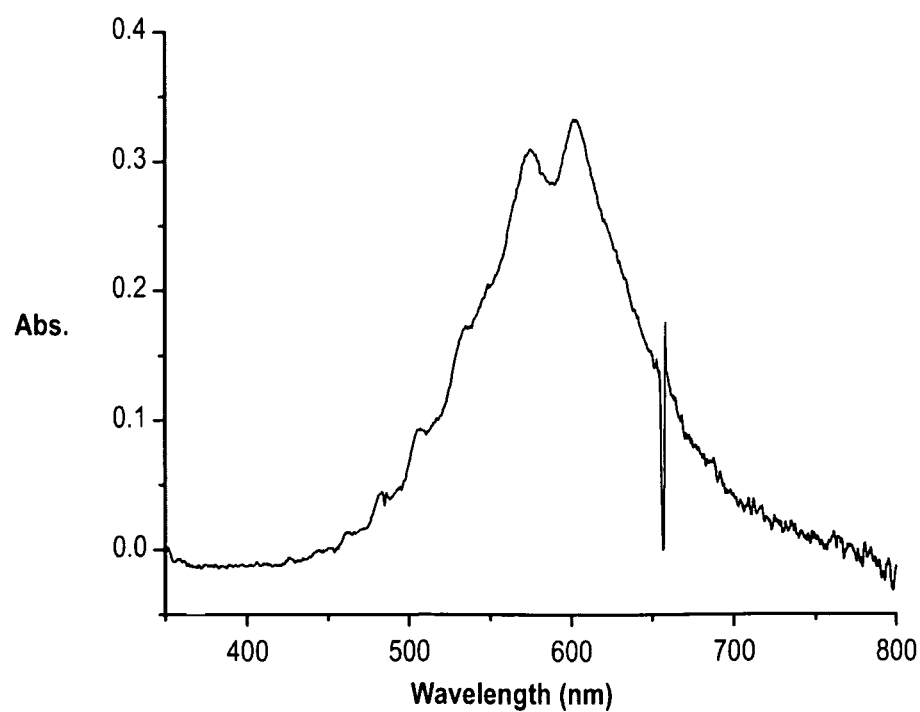

Ozone has two absorption bands in the UV/Visible region; a strong band with $\lambda_{max}=253.7$ nm and a weaker band with two maxima at 577 nm and 603 nm (FIGS. 4A and 4B, respectively). The intensity of the light absorbed by ozone at these wavelengths is directly proportional to the concentration of the ozone, and therefore absorption values can be used as a measure of the ozone concentration. The Chappuis band in the visible region was chosen because its intensity gave suitable absorption values at the ozone concentrations studied.

The absorbance at 580 nm was measured for a solution of ozone in liquid carbon dioxide (T=5.0±0.2° C. or 277.15±0.2 K, P=63.4±1.4 bar). A known volume (0.52 mL) of this solution was then sampled in a stainless steel tube (FIG. 3). This sample was allowed to expand slowly to room temperature and pressure (R.T.P.) and the escaping gas was bubbled through an aqueous solution of potassium iodide. The tubing was then flushed with compressed air, which was also bubbled through a KI solution. The KI solution was titrated with $4\times10^{-4}$ mol dm$^{-3}$ $Na_2S_2O_3$ to determine the iodine concentration. The slight drop in cell pressure was compensated for by pumping in more $O_3/O_2$ gas mixture and the procedure was repeated three times. Values of $\epsilon$ are shown in Table 1.

TABLE 1

| Run | Concentration $O_3$ in 0.52 ml sample (mol dm$^{-3}$) | Abs. at 580 nm | $\epsilon$ (dm$^3$ mol$^{-1}$ cm$^{-1}$) |
| --- | --- | --- | --- |
| 1 | 2.11 × 10$^{-3}$ | 0.159 | 29.6 |
| 2 | 1.69 × 10$^{-3}$ | 0.137 | 25.4 |
| 3 | 3.02 × 10$^{-3}$ | 0.201 | 26.2 |
| 4 | 2.98 × 10$^{-3}$ | 0.184 | 24.3 |

4.

Figure 5:
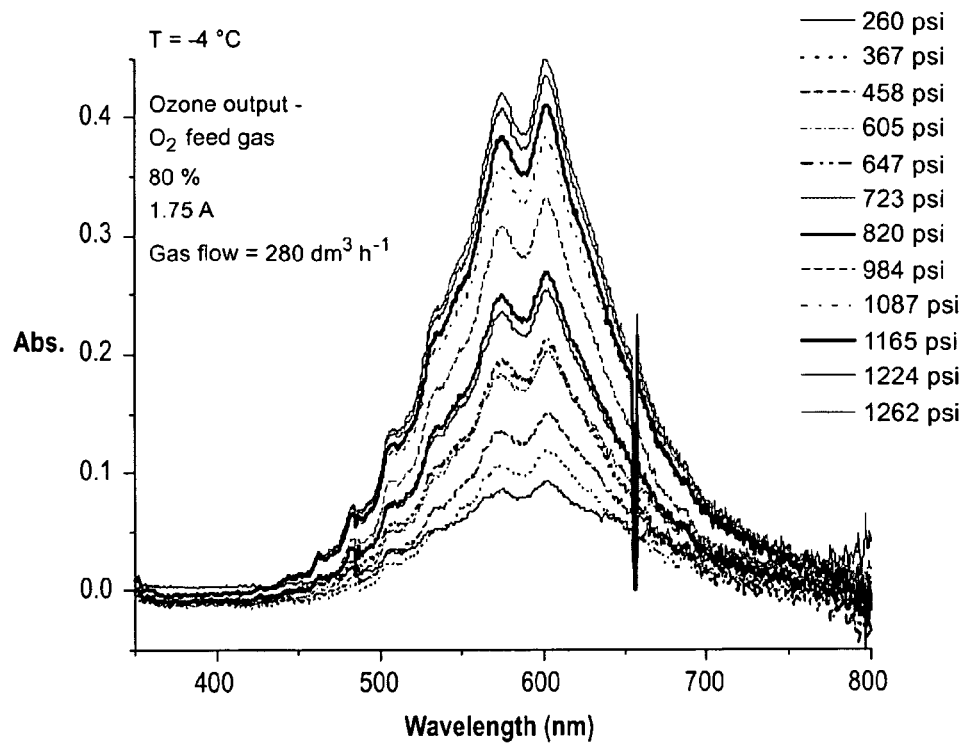
FIG. 5 is a graph showing the increase in absorption in the Chappuis Band as ozone is added (by pressurization) to a fixed volume of liquid $CO_2$.
Figure 6:
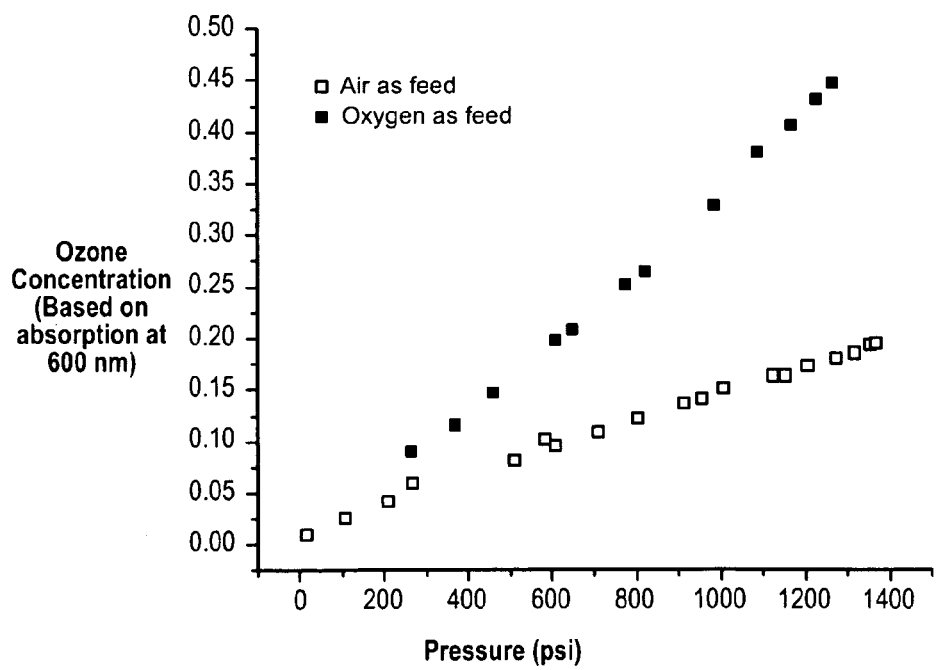
FIG. 6 is a graph showing ozone concentration vs $P_{total}$ as ozone/air or ozone/oxygen mixtures are added (by pressurization) to a fixed volume of liquid $CO_2$.

When the gaseous output of the ozone generator is compressed into the reaction cell using the syringe pump, the concentration of ozone increases linearly with the total pressure (assuming ideal gas behavior at the ISCO pump conditions). Since the mole fraction of ozone in the output stream is constant, $P_{O_3}$ should increase proportionally with the total pressure. This behavior is confirmed in FIGS. 5 and 6 for both $O_2$ and air as source gases for ozone production.

5.

Figure 7:
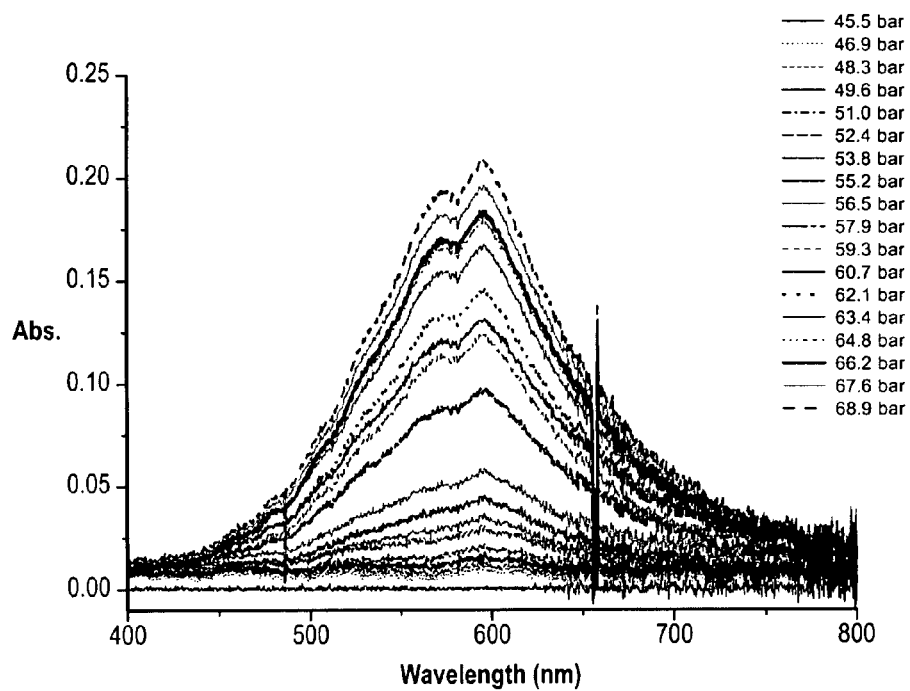
FIG. 7 is a graph showing the increase in absorption in the Chappuis Band as ozone is added to liquid carbon dioxide.
Figure 8:
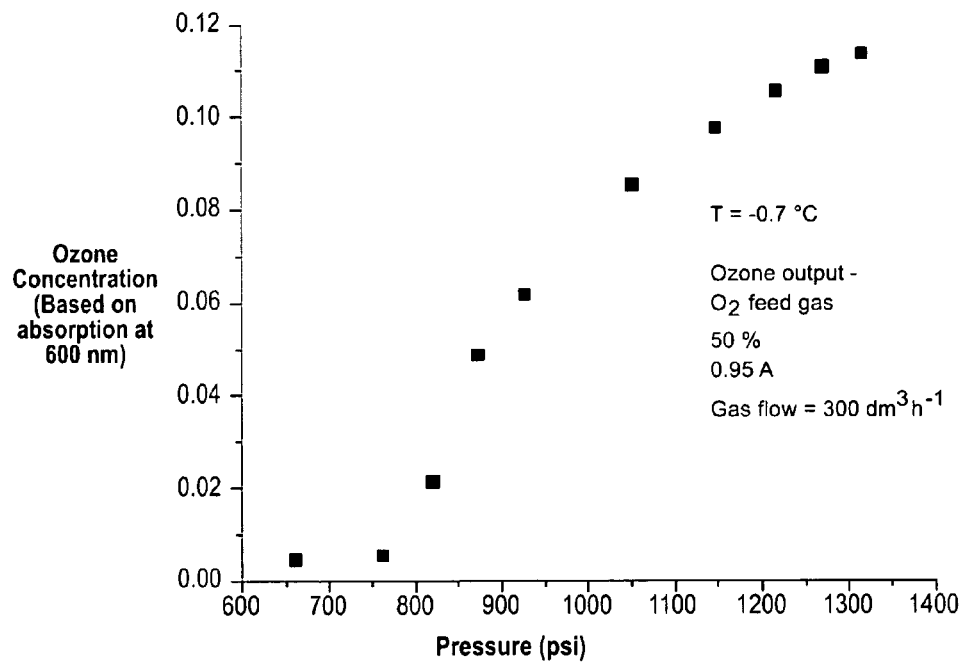
FIG. 8 is a graph showing ozone concentration vs $P_{total}$ as ozone is added to liquid $CO_2$.

When measuring the concentration of ozone dissolved in liquid carbon dioxide at −0.7° C. (or 272.45 K), such linear behavior is not observed (FIGS. 7 and 8). A volume of liquid $CO_2$ is introduced into the cell so that the gas/liquid interface is sufficiently high in the cell and the light path of the spectrophotometer is in the liquid phase throughout the experiments. The gas output from the ozone generator is then compressed using the syringe pump and the ozone mixture is pumped into the liquid carbon dioxide through a titanium frit to ensure good mixing. The ozone concentration in the liquid $CO_2$ is then measured spectrophotometrically after allowing a period of time for equilibrium to be reached. As the critical pressure of ozone is approached (808 psi, 55.7 bar), there is a significant increase in the quantity of ozone dissolved in the liquid carbon dioxide. At 53.1 bar, the ozone concentration in the liquid phase is approximately 0.005 unit. At 62.1 bar however, the $O_3$ concentration in the liquid phase is 0.05 unit, dramatically enhanced by more than order of magnitude. Similar behavior is observed over a range of temperatures.

6.

The use of CXLs has many advantages over the use of conventional neat solvents. By replacing a significant fraction of conventional organic solvents with carbon dioxide, the CXL mixtures enhance mass transfer and reaction rates, reduce waste, and make reactors inherently safer. Additionally, many classes of substrates have higher solubility in CXLs than in pure liquid or supercritical carbon dioxide. A CXL is created by expanding a conventional solvent with pressurized carbon dioxide to create a single phase mixture in which a measurable fraction of the liquid volume is attributable to the compressed carbon dioxide. The photograph data (not shown) indicate that the expansion of methanol to form a CXL. The meniscus shows that the total volume has increased by approximately 120% under these conditions (52.7 bar of carbon dioxide).

7.

Figure 9:
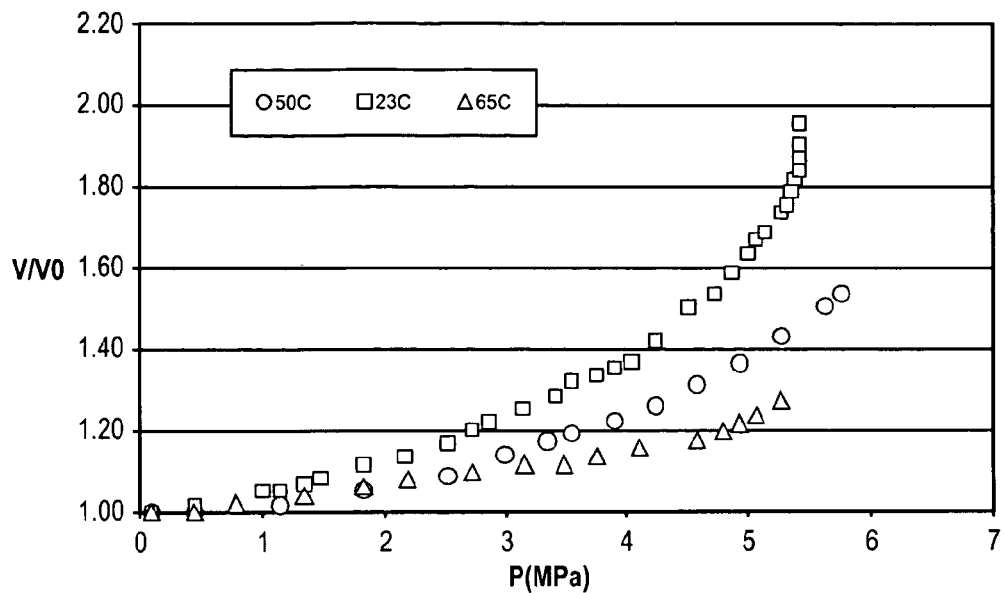
FIG. 9 is a graph showing the effect of temperature on the $CO_2$ expansion of methanol/soybean oil binary (molar ratio of 6:1).

The effect of temperature on $CO_2$ expansion of a methanol/soybean oil binary composition was studied. The $CO_2$ was used to expand a 6:1 methanol soybean binary composition at 296.15 K, 323.15 K and 338.15 K. As shown in FIG. 9, the temperature at 296 K had a more significant change in V/Vo as the pressure was increased. The miscibility of $CO_2$ with the methanol+soybean binary mixture provides the opportunity to seek enhanced ozone solubility and safe selective biomass oxidation in this CXL system, as indicated above.

8.

Figure 10:
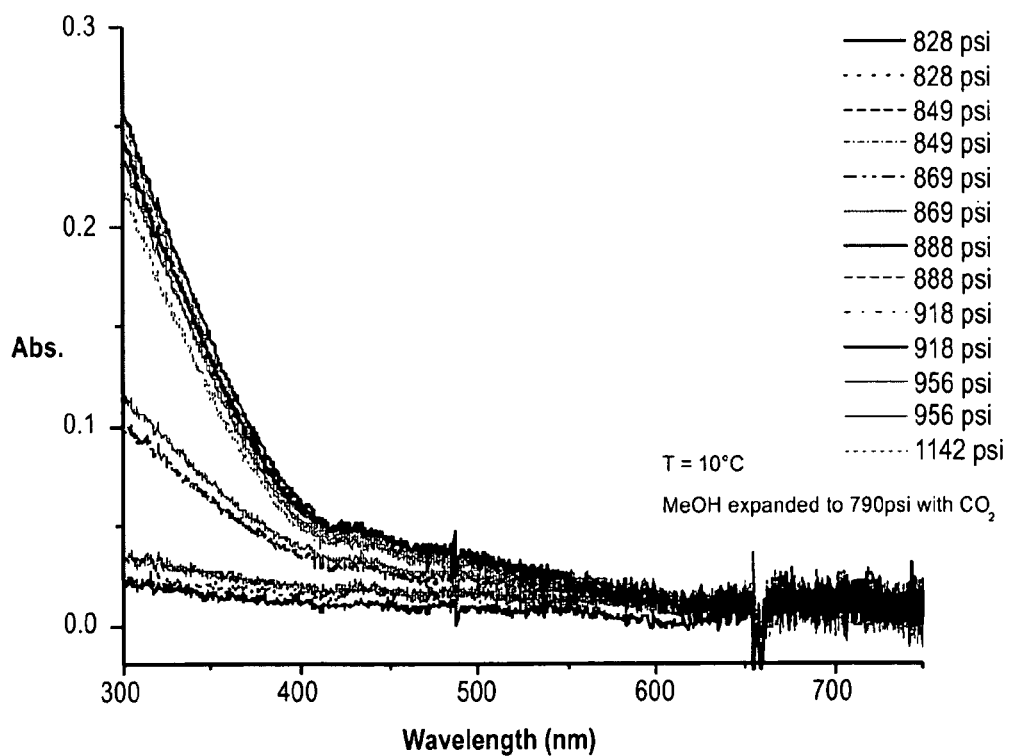
FIG. 10 is a graph showing the UV/Visible spectra of CXL methanol as ozone is added.
Figure 11:
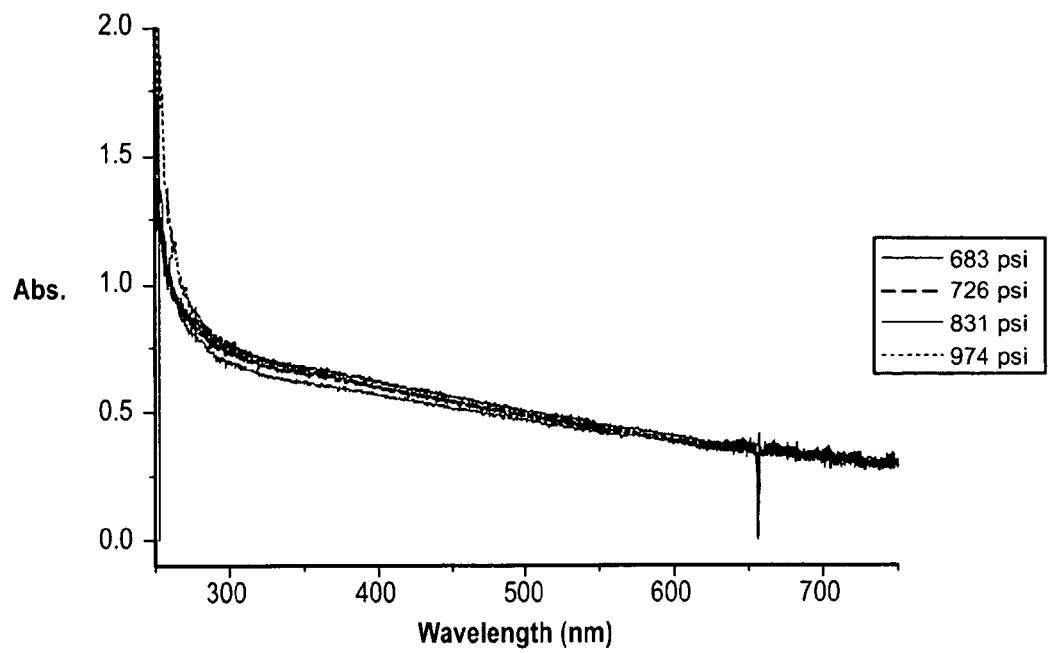
FIG. 11 is a graph showing the UV/Visible spectra of CXL hexane as ozone is added.
Figure 12:
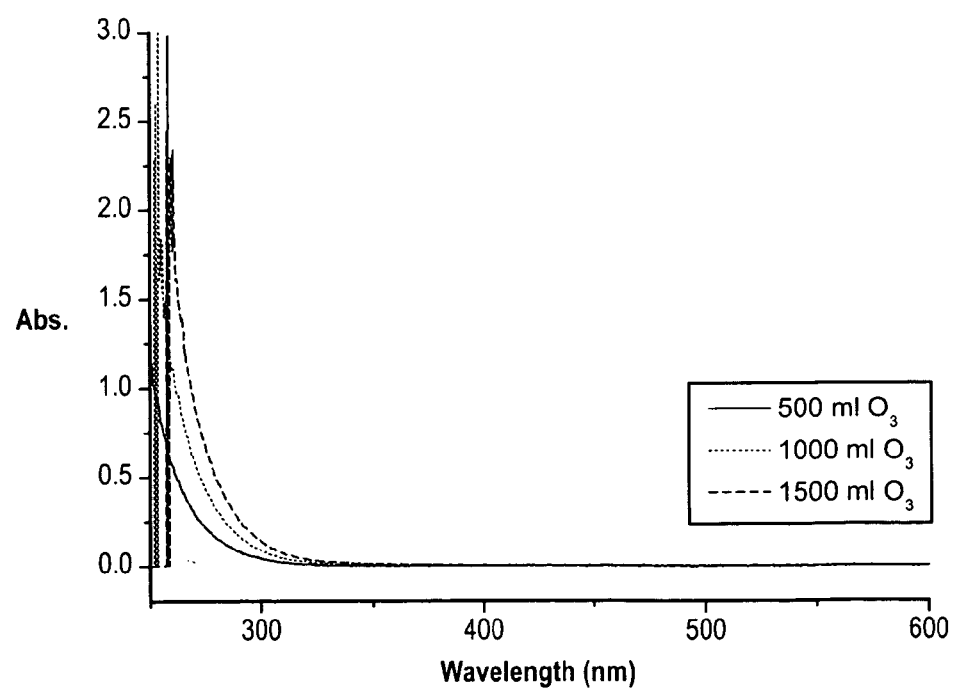
FIG. 12 is a graph showing the UV/Visible spectra of liquid methanol at 1.013 bar as ozone is added.
Figure 13:
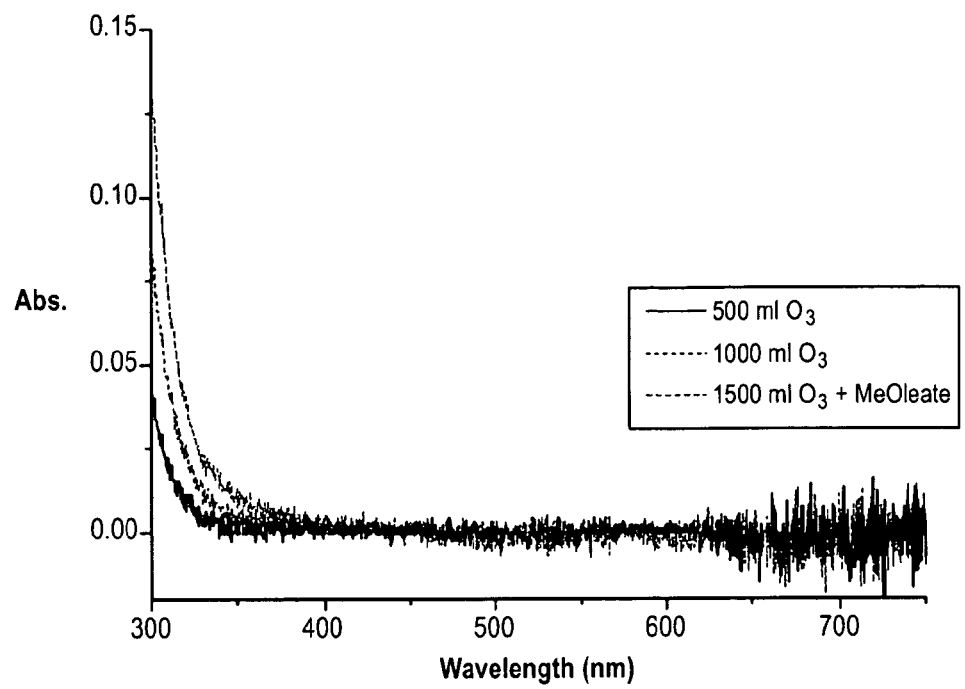
FIG. 13 is a graph showing the UV/Visible spectra of ozonated methanol as methyl oleate is added.
Figure 14:
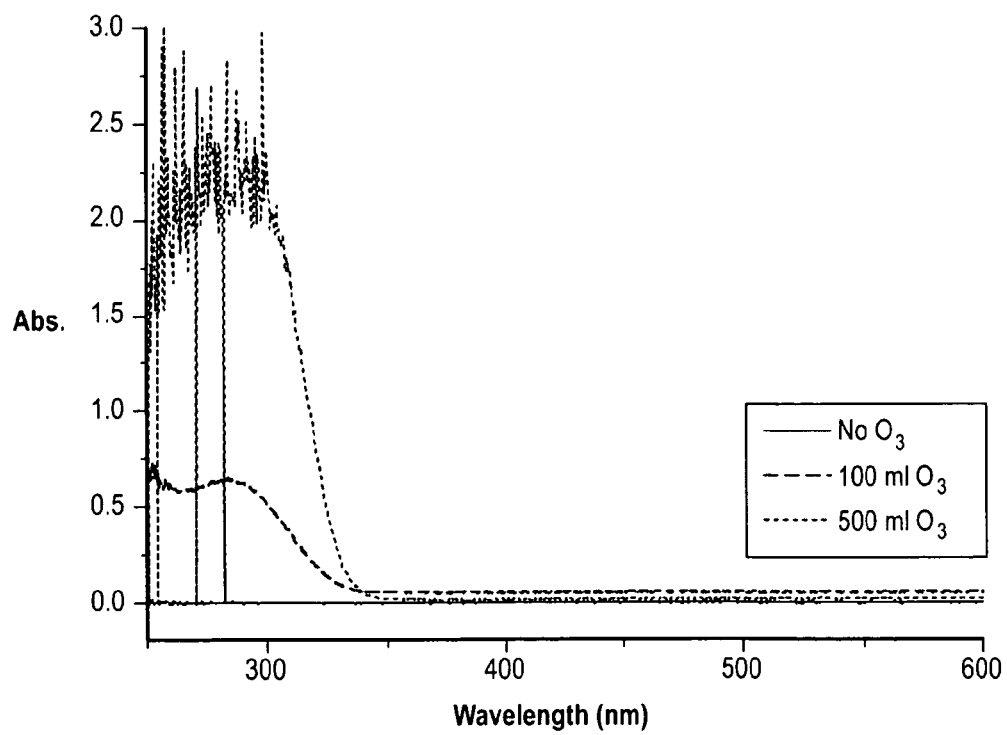
FIG. 14 is a graph showing the UV/Visible spectra of methyl oleate in methanol as ozone is added.

Utilizing the advantages of CXLs for ozonolysis reactions is an attractive goal. However, studies have demonstrated that the choice of solvent to be expanded with carbon dioxide is important, since the reactivity of ozone is such that it will rapidly oxidize many organic solvents at the elevated pressures required to form the CXL. When ozone is added to $CO_2$ expanded methanol the characteristic ozone bands in the UV/Visible spectra are not observed (FIG. 10). The same observation is made when ozone is added to a hexane CXL (FIG. 11). It has been widely reported, however, that ozonolysis reactions can be conducted in organic solvents, particularly methanol. Our attempts to measure ozone concentrations in neat methanol at 1.013 bar and −4° C. (268.15 K) show no measurable concentration of dissolved ozone in the solvent (FIG. 12; T=276.15 K, P=1.013 bar, 1500 mL ozone solution 50%, 1.0 A; $O_2$ source @ 200 cfm, ozone bubbled through solvent). Furthermore, addition of the substrate methyl oleate to a sample of methanol through which ozone had been bubbled, showed no evidence of reaction (FIG. 13). However, the UV/Visible spectra (FIG. 14; T=276.15 K, P=1.013 bar, 0.5 mL methyl oleate in 9 mL methanol) taken following the addition of ozone to a methanolic solution of methyl oleate, indicate the formation of a product with a strong absorption band in the UV region ($\lambda_{max}=284$ nm). These observations indicate that ozone readily oxidizes methanol, but, kinetically, the reaction with methyl oleate is preferred. This can provide an indication that the substrate that is the solvent can be the target of ozone oxidation (e.g., methyl oleate as the substrate and solvent).

9.

Ozonolysis experiments were conducted on various substrates. In a typical substrate ozonolysis experiment, the substrate is introduced into the reaction cell maintained at ambient pressure and the desired reaction temperature, following which $CO_2$ is added to create a liquid phase. Using the ISCO pump, the ozone containing gas is then pumped into the reaction cell to a predetermined pressure above that of the $CO_2$/substrate mixture. The ozone concentration is followed spectrophotometrically during the reaction. At the end of the batch reaction, samples are withdrawn from the $CO_2$ liquid phase by depressurizing the effluent to a cold trap (maintained at −78° C. or 195.15 K) in which the samples are collected and subsequently analyzed using GC/MS.

10.

The concentration of ozone dissolved in water was measured using UV/Visible spectrophotometry as increasing pressures of a gaseous mixture of $O_2$ and $O_3$ were applied. The intensity of the light absorbed by ozone at 580 nm is directly proportional to the concentration of the ozone and therefore absorption values can be used as a measure of the ozone concentration. In a typical measurement, water was introduced into the view cell so that the gas liquid interface was well above the light path of the Ocean Optics Fiber Optic spectrophotometer. The cell was then sealed and the temperature allowed to equilibrate. Temperature was controlled using a refrigerated bath circulating a heat transfer fluid through an aluminum jacket in thermal contact with the view cell. The gaseous output of the ozone generator was then compressed and pumped into the view cell using the ISCO syringe pump. Spectrophotometric measurements were taken as the pressure was increased. After each increase in pressure, the cell contents were thoroughly stirred, using a magnetic stirrer bar, for at least two minutes before a spectrophotometric measurement was taken.

Figure 15:
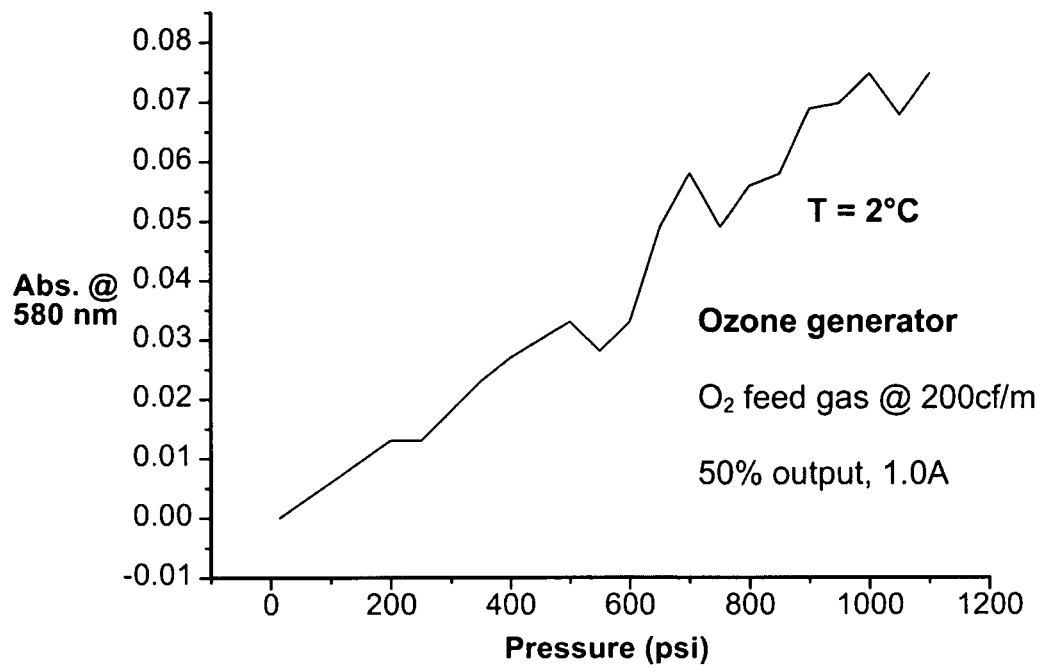
FIG. 15 is a graph showing a measure of ozone solubility in water as a function of pressure under isothermal conditions when the temperature is 2° C.
Figure 16:
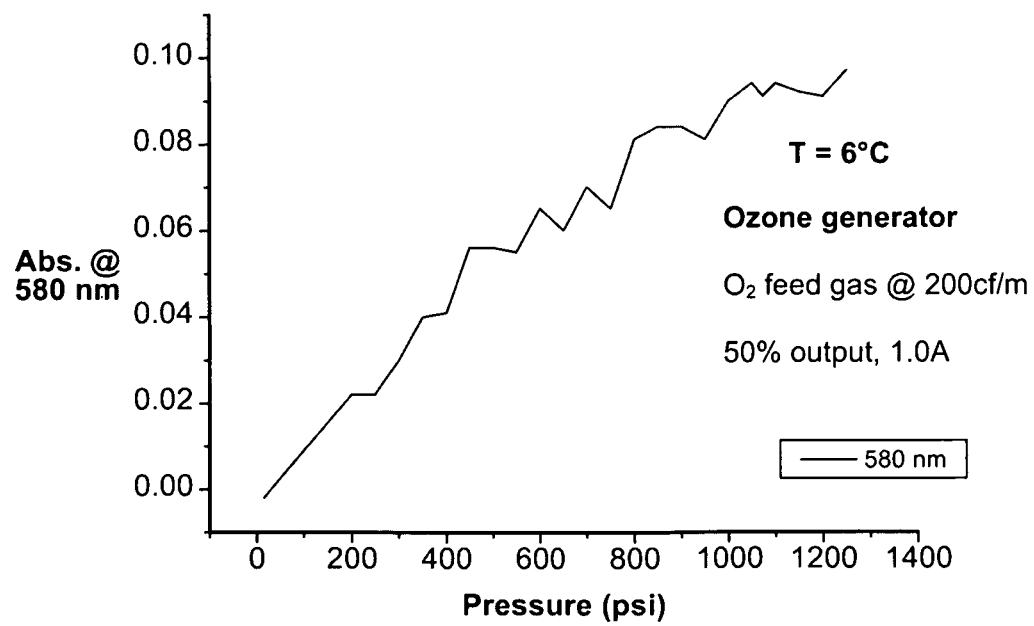
FIG. 16 is a graph showing a measure of ozone solubility in water as a function of pressure under isothermal conditions when the temperature is 6° C.
Figure 17:
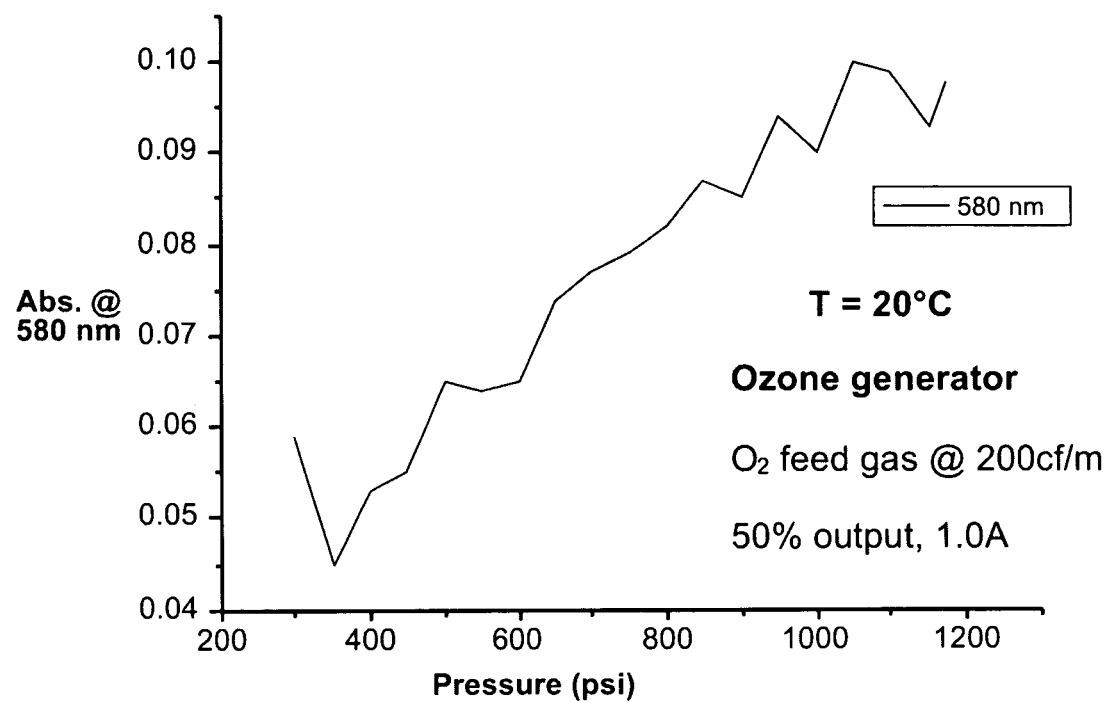
FIG. 17 is a graph showing a measure of ozone solubility in water as a function of pressure under isothermal conditions when the temperature is 20° C.

The spectra recorded at a series of pressures and temperatures (FIGS. 15, 16, and 17) clearly show that the concentration of ozone dissolved in water increases linearly as a function of pressure. There is no sharp enhancement of ozone concentration in water, as there is in liquid carbon dioxide, as the pressure increases through the critical pressure of ozone (808 psi, 55.7 bar).

11.

In a typical experiment, a known quantity of the olefinic substrate was placed in a high pressure reaction cell and carbon dioxide was added to a pressure of 44.8 bar. The solution was cooled to the reaction temperature and then a gaseous mixture of ozone and oxygen was added to the reaction cell using an ISCO syringe pump until at least a twofold excess of ozone had been added. The mixture was left to react, with stirring, for several hours. Product collection was performed by slowly venting the liquid $CO_2$ portion of the mixture through a cold (0° C. or 273.15 K) trap consisting of methanol, hexane or dichloromethane. The cell was then re-pressurized with $CO_2$ and vented through the trap a second time. The cell was then washed twice with the collection solvent. Product analysis was performed by GC/MS with relevant internal standards. Major products for each substrate studied are shown in Table 2.

TABLE 2

| Substrate | Mixing | Conversion | Products |
|---|---|---|---|
| methyl oleate (insoluble in liquid $CO_2$) | mechanical | 24% | nonanal nonanedioic acid, monomethyl ester nonanoic acid |
| methyl oleate | ultrasonic | 100% | nonanal 9-oxo-nonanoic acid, methyl ester nonanedioic acid, monomethyl ester nonanoic acid |
| trans-stilbene (soluble in liquid $CO_2$) | mechanical | 95% | benzaldehyde, benzoic acid, benzoic acid, ethyl ester phenol 2-hexanone |
| cis-stilbene (soluble in liquid $CO_2$) | mechanical | 85% | benzaldehyde benzoic acid phenol |
| cyclohexene | mechanical | 99% | polymer hexanoic acid 1,1′oxybis(hexane) |
| propylene | mechanical |  | polymer acetic acid cyclopentanol |
| ferulic acid | ultrasonic | >80% | 4-hydroxy-3-methoxy-benzaldehyde phenol |

Figure 18:
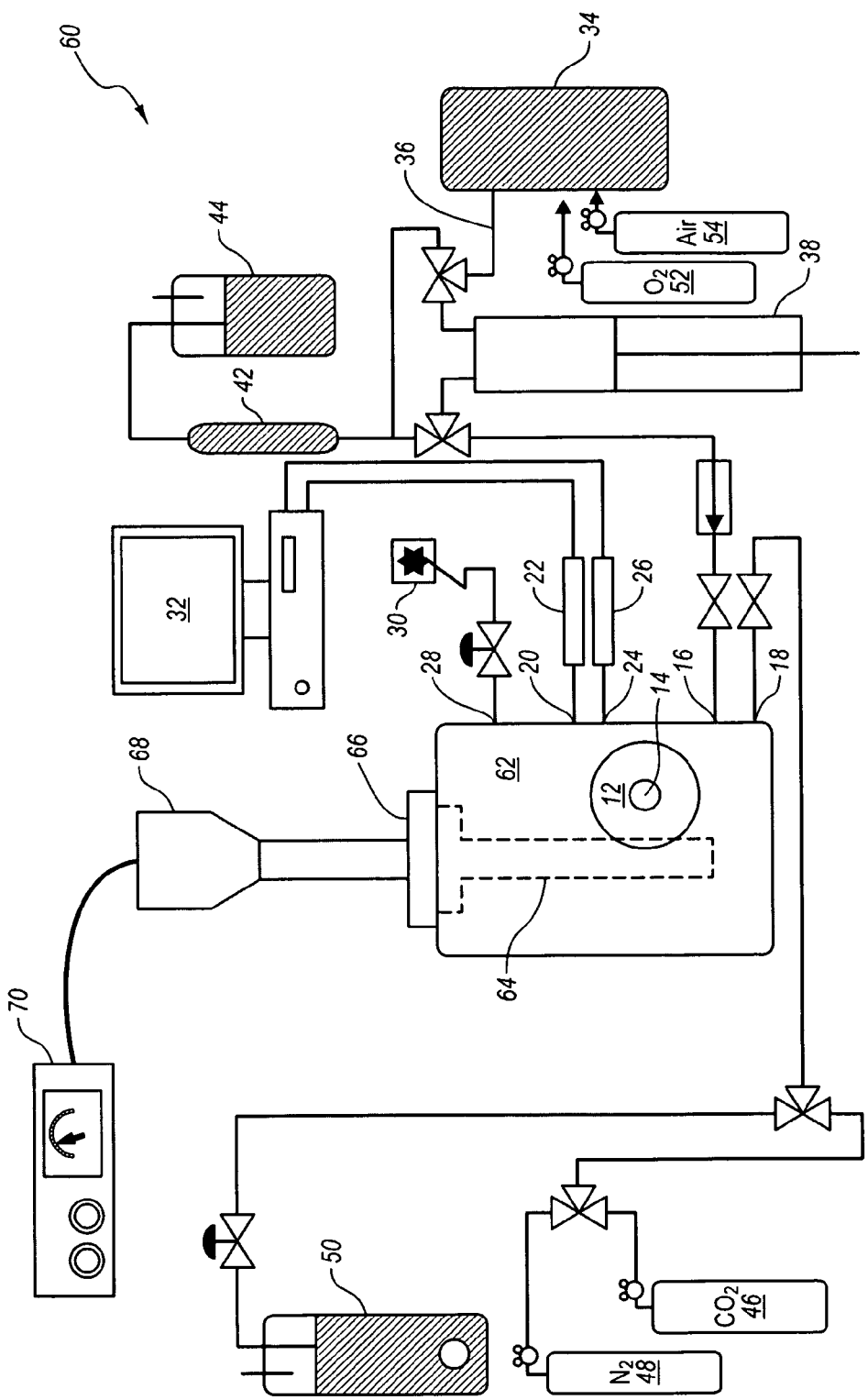
FIG. 18 is a schematic diagram of a system that has an ultrasonic probe for causing ultrasonic agitation during ozonolysis or when purifying ozone from a gas.

As shown in FIG. 18, a high pressure reaction system 60 was constructed. The high pressure reaction system 60 can include many of the features shown in FIG. 3. The high pressure reaction system 60 additionally includes a high pressure titanium reaction cell 62, incorporating an ultrasonic probe 64 (FIG. 18). The ultrasonic probe 64 extends into the reaction cell 62 and is coupled thereto with a retaining plate 66. The retaining plate is further coupled to an ultrasonic transducer 68 that receives high frequency input from a signal generator 70 for the ultrasonic probe 64.

The reaction system 60 was used to create emulsions of insoluble substrate in liquid $CO_2$ in order to enhance the interphase mass transfer area for reaction between the substrate and $O_3$. The stability of ozone, when ozone-containing solutions were subjected to ultrasonic mixing, was also investigated.

Figures 19, 20:
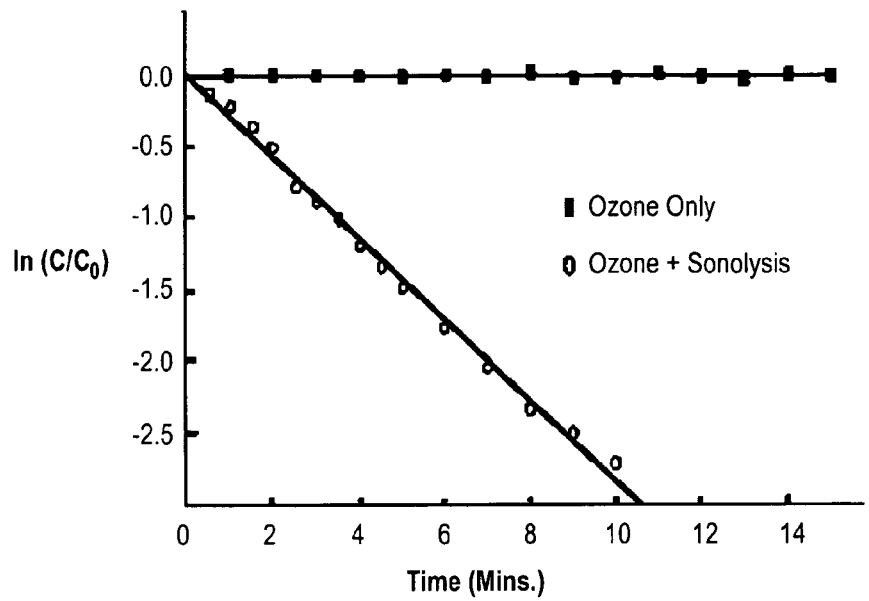
FIG. 19 is a graph showing the rate of ozone decomposition in water with and without ultrasonic agitation (Kang, J-W., Lee, K-H., Koh, C-I., Nam, S-N., *Korean Journal of Chemical Engineering* 18 336 (2001)).
FIG. 20 is a table showing the effects of ultrasonic agitation on the rate constants for ozone decomposition in water and in liquid carbon dioxide.

In water, ultrasonic agitation was shown to increase the rate of ozone decomposition by at least two orders of magnitude as shown in FIG. 19 (Kang, J-W., Lee, K-H., Koh, C-I., Nam, S-N., *Korean Journal of Chemical Engineering* 18 336 (2001)). Our research has shown that there is no such effect using dense phase carbon dioxide (FIG. 20), probably due to the absence of the free radical propagation steps typical of the mechanism of ozone decomposition in water.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein in their entirety by specific reference.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of performing ozonolysis on a molecule in a liquid, the method comprising:
    providing a composition having a liquid and ozone, wherein the liquid and ozone composition has a temperature between about 0.9 to 1.35 times the critical temperature of ozone wherein the temperature is expressed in absolute units and a pressure between about 0.5 to 2 times the critical pressure of ozone such that the ozone is sharply compressed to selectively dissolve into the liquid while background gases do not display a sharp increase in compressibility, wherein the molecule is dissolved or dispersed in the liquid; and
    reacting the molecule with the ozone.

2. A method as in claim 1, further comprising:
    introducing the ozone into the liquid, wherein the liquid and ozone combination has a temperature between about 0.9 to 1.35 times the critical temperature of ozone; and
    increasing, isothermally, the pressure of the ozone in the liquid to about 0.5 to 2 times the critical pressure of ozone so as to increase the ozone concentration in the liquid.

3. A method as in claim 2, further comprising introducing the molecule into one of the following:
    the liquid before the ozone;
    the ozone before the liquid; or
    the liquid and ozone combination.

4. A method as in claim 3, wherein the liquid is comprised of liquid carbon dioxide, light hydrocarbons ($C_4$ or lower), methanol, ethanol, alcohols, hexane, $SF_6$, xenon, water, fluorocarbon solvents, highly oxygenated molecules, highly fluorinated molecules, $CF_3CO_2H$, ionic liquids, strong liquid acids, $H_2SO_4$, $HSO_3F$, $HSO_3CF_3$, organic acids, saturated hydrocarbons, or combinations thereof.

5. A method as in claim 3, wherein the liquid is a carbon dioxide expanded liquid comprised of light hydrocarbons ($C_4$ or lower), methanol, ethanol, alcohols, hexane, $SF_6$, xenon, water, fluorocarbon solvents, highly oxygenated molecules, highly fluorinated molecules, $CF_3CO_2H$, ionic liquids, strong liquid acids, $H_2SO_4$, $HSO_3F$, $HSO_3CF_3$, organic acids, saturated hydrocarbons, or combinations thereof.

6. A method as in claim 3, where the molecule is selected from the group consisting of a molecule having an unsaturated hydrocarbon, a molecule having a carbon-carbon double bond, unsaturated hydrocarbon acids, methyl oleate, oils, fats, soybean oil, unsaturated fatty acids, vegetable fatty acids, esters of fatty acids, fatty acid amides, alkenes, steroids, benzylics, a molecule having an allylic moiety, terpenes, cephalosporin, cephalosporin derivatives, and a tertiary allylic alcohol.

7. A method as in claim 2 wherein said step of introducing the ozone into the liquid is such that the liquid and ozone combination has a temperature between about 0.95 and about 1.25 times the critical temperature of ozone.

8. A method as in claim 2 wherein said step of increasing the pressure of the ozone in the liquid comprises the step of increasing the pressure to about 0.75 to about 1.5 times the critical pressure of ozone so as to increase the ozone concentration in the liquid.

9. A method as in claim 2 wherein said step of increasing the pressure of the ozone in the liquid comprises the step of increasing the pressure to about 0.9 to about 1.35 times the critical pressure of ozone so as to increase the ozone concentration in the liquid.

10. A method as in claim 2 wherein said step of increasing the pressure of the ozone in the liquid comprises the step of increasing the pressure to about 0.95 to about 1.25 times the critical pressure of ozone so as to increase the ozone concentration in the liquid.

11. A method as in claim 1, further comprising providing ultrasonic agitation to the liquid and ozone.

12. A method as in claim 1 wherein the liquid is liquid carbon dioxide and wherein the liquid carbon dioxide and ozone combination has an absorption band at $\lambda_{max}$ at about 253.7 nm and at about 577 nm and 603 nm, wherein at least one of the $\lambda_{max}$ has an absorbance unit of about 0.005 unit when the pressure is below about 0.5 times the critical pressure of ozone and the $\lambda_{max}$ has an absorbance unit of about 0.01 to about 0.1 when the pressure is between about 0.5 to about 2 times the critical pressure of ozone.

13. A method as in claim 1 wherein the liquid is a carbon dioxide-expanded solvent and wherein the carbon dioxide-expanded organic solvent and ozone combination has an absorption band at $\lambda_{max}$ at about 253.7 nm and at about 577 nm and 603 nm, wherein at least one of the $\lambda_{max}$ has an absorbance unit of about 0.005 unit when the pressure is below about 0.5 times the critical pressure of ozone and the $\lambda_{max}$ has an absorbance unit of about 0.01 to about 0.1 when the pressure is between about 0.5 to about 2 times the critical pressure of ozone.

14. A method as in claim 1, wherein the liquid is liquid carbon dioxide.

15. A method as in claim 1, wherein the liquid is a carbon dioxide-expanded liquid.

16. A method as in claim 1, where the molecule is a fatty acid or ester thereof.

17. A method as in claim 1, where the molecule is selected from the group consisting of butyric acid, caproic acid, caprylic acid, capric acid, lauric acid, myristic acid, palmitic acid, stearic acid, arachic acid, behenic acid, lignoceric acid, hexacosanoic acid, octacosanoic acid, triacontanoic acid and n-dotriacontanoic acid, propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid, heptacosanoic acid, isobutyric acid, isocaproic acid, isocaprylic acid, isocapric acid, isolauric acid, 11-methyl-dodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, α-ethyl-hexanoic acid, α-hexyl-decanoic acid, α-heptylundecanoic acid, 2-decyltetradecanoic acid, 2-undecyltetradecanoic acid, 2-decylpentadecanoic acid, 2-undecylpentadecanoic acid, 6-methyl-octanoic acid, 8-methyl-decanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic, 26-methyloctacosanoic acid, including 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid (18:3 n3), gamma linolenic acid (18:3 n6), a-eleostearic acid, gadoleic acid (20:1), α-eleostearic acid, punicic acid, 6,9,12,15-octadecatetraenoic acid, parinaric acid, 5,8,11,14-eicosatetraenoic acid, erucic acid, 5,8,11,14,17-eicosapentaenoic acid, 7,10,13,16,19-docosapentaenoic acid, 4,7,10,13,16,19-docosahexaenoic acid, α-hydroxylauric acid, α-hydroxy-myristic acid, α-hydroxypalmitic acid, α-hydroxystearic acid, ω-hydroxylauric acid, α-hydroxyarachic acid, 9-hydroxy-12-octadecenoic acid, ricinoleic acid, α-hydroxybehenic acid, 9-hydroxy-trans-10,12-octadecadienic acid, kamolenic acid, ipurolic acid, 9,10-dihydroxystearic acid, 12-hydroxystearic acid, oxalic acid, citric acid, malonic acid, succinic acid, glutaric acid, adipic acid, pimelic acid, suberic acid, azelaic acid, sebacic acid, and D,L-malic acid, or combinations thereof.

18. A method as in claim 1, where the molecule is selected from the group consisting of methyl laurate, methyl myristate, methyl palmitate, methyl oleate, methyl elaidate, methyl linoleate, methyl linolenate, methyl stearate, methyl erucate, methyl ricinoleate, methyl licanate, methyl elaeostearate, methyl arachidonate, methyl clupanodonate, ethyl laurate, ethyl myristate, ethyl palmitate, ethyl oleate, ethyl elaidate, ethyl linoleate, ethyl linolenate, ethyl stearate, ethyl erucate, ethyl ricinoleate, ethyl lincanate, ethyl elaeostearate, ethyl arachidonate, ethyl clupanodonate, propyl laurate, propyl myristate, propyl palmitate, propyl oleate, propyl elaidate, propyl linoleate, propyl linolenate, propyl stearate, propyl erucate, propyl ricinoleate, propyl licanate, propyl elaeostearate, propyl arachidonate, propyl clupanodonate, isopropyl laurate, isopropyl myristate, isopropyl palmitate, isopropyl oleate, isopropyl elaidate, isopropyl linoleate, isopropyl linolenate, isopropyl stearate, isopropyl erucate, isopropyl ricinoleate, isopropyl licanate, isopropyl elaeostearate, isopropyl arachidonate, isopropyl clupanodonate, butyl laurate, butyl myristate, butyl palmitate, butyl oleate, butyl elaidate, butyl linoleate, butyl linolenate, butyl stearate, butyl erucate, butyl ricinoleate, butyl licanate, butyl elaeostearate, butyl arachidonate, butyl clupanodonate, sec.butyl laurate, sec.butyl myristate, sec.butyl palmitate, sec.butyl oleate, sec.butyl elaidate, sec.butyl linoleate, sec.butyl linolenate, sec.butyl stearate, sec.butyl erucate, sec.butyl ricinoleate, sec.butyl licanate, sec.butyl elaeostearate, sec.butyl arachidonate, sec.butyl clupanodonate, isobutyl laurate, isobutyl myristate, isobutyl palmitate, isobutyl oleate, isobutyl elaidate, isobutyl linoleate, isobutyl linolenate, isobutyl stearate, isobutyl erucate, isobutyl ricinoleate, isobutyl licanate, isobutyl elaeostearate, isopropyl arachidonate, isobutyl clupanodonate, amyl laurate, amyl myristate, amyl palmitate, amyl oleate, amyl elaidate, amyl linoleate, amyl linolenate, amyl stearate, amyl erucate, amyl ricinoleate, amyl licanate, amyl elaeostearate, amyl arachidonate, amyl clupanodonate, hexyl laurate, hexyl myristate, hexyl palmitate, hexyl oleate, hexyl elaidate, hexyl linoleate, hexyl linolenate, hexyl stearate, hexyl erucate, hexyl ricinoleate, hexyl licanate, hexyl elaeostearate, hexyl arachidonate, hexyl clupanodonate, heptyl laurate, heptyl myristate, heptyl palmitate, heptyl oleate, heptyl elaidate, heptyl linoleate, heptyl linolenate, heptyl stearate, heptyl erucate, heptyl ricinoleate, heptyl lincanate, heptyl elaeostearate, heptyl arachidonate, heptyl clupanodonate, octyl laurate, octyl myristate, octyl palmitate, octyl oleate, octyl elaidate, octyl linoleate, octyl linolenate, octyl stearate, octyl erucate, octyl ricinoleate, octyl licanate, octyl elaeostearate, octyl arachidonate, octyl clupanodonate, 2-ethylhexyl laurate, 2-ethylhexyl myristate, 2-ethylhexyl palmitate, 2-ethylhexyl oleate, 2-ethylhexyl elaidate, 2-ethylhexyl linoleate, 2-ethylhexyl linolenate, 2-ethylhexyl stearate, 2-ethylhexyl erucate, 2-ethylhexyl ricinoleate, 2-ethylhexyl licanate, 2-ethylhexyl elaeostearate, 2-ethylhexyl arachidonate, 2-ethylhexyl clupanodonate, t-butyl laurate, t-butyl myristate, t-butyl palmitate, t-butyl oleate, t-butyl elaidate, t-butyl linoleate, t-butyl linolenate, t-butyl stearate, t-butyl erucate, t-butyl ricinoleate, t-butyl licanate, t-butyl elaeostearate, t-butyl arachidonate, t-butyl clupanodonate, isooctyl laurate, isooctyl myristate, isooctyl palmitate, isooctyl oleate, isooctyl elaidate, isooctyl linoleate, isooctyl linolenate, isooctyl stearate, isooctyl erucate, isooctyl ricinoleate, isooctyl licanate, isooctyl elaeostearate, isooctyl arachidonate, isooctyl clupanodonate, nonyl laurate, nonyl myristate, nonyl palmitate, nonyl oleate, nonyl elaidate, nonyl linoleate, nonyl linolenate, nonyl stearate, nonyl erucate, nonyl ricinoleate, nonyl licanate, nonyl elaeostearate, nonyl arachidonate, nonyl clupanodonate, decyl laurate, decyl myristate, decyl palmitate, decyl oleate, decyl elaidate, decyl linoleate, decyl linolenate, decyl stearate, decyl erucate, decyl ricinoleate, decyl licanate, decyl elaeostearate, decyl arachidonate, decyl clupanodonate, undecyl laurate, undecyl myristate, undecyl palmitate, undecyl oleate, undecyl elaidate, undecyl linoleate, undecyl linolenate, undecyl stearate, undecyl erucate, undecyl ricinoleate, undecyl licanate, undecyl elaeostearate, undecyl arachidonate, undecyl clupanodonate, dodecyl laurate, dodecyl myristate, dodecyl palmitate, dodecyl oleate, dodecyl elaidate, dodecyl linoleate, dodecyl linolenate, dodecyl stearate, dodecyl erucate, dodecyl ricinoleate, dodecyl licanate, dodecyl elaeostearate, dodecyl arachidonate, dodecyl clupanodonate, methyl brasidate, ethyl brasidate, propyl brasidate, isopropyl brasidate, butyl brasidate, sec-butyl braisidate, isobutyl brasidate, t-butyl brasidate, amyl brasidate, hexyl brasidate, heptyl brasidate, octyl brasidate, 2-ethylhexyl brasidate, isooctyl brasidate, nonyl brasidate, decyl brasidate, undecyl brasidate, dodecyl brasidate, hydroxyethyl laurate, hydroxyethyl myristate, hydroxyethylpalmitate, hydroxyethyl oleate, hydroxyethyl elaidate, hydroxyethyl linoleate, hydroxyethyl linolenate, hydroxyethyl stearate, hydroxyethyl erucate, hydroxyethyl ricinoleate, hydroxyethyl licanate, hydroxyethyl elaeostearate, hydroxyethyl arachidonate, hydroxyethyl clupanodonate, hydroxyethyl brasidate, polyethoxylated lauric acid, polyethoxylated myristic acid, polyethoxylated palmitic acid, polyethoxylated oleic acid, polyethoxylated elaidic acid, polyethoxylated linoleic acid, polyethoxylated linolenic acid, polyethoxylated stearic acid, polyethoxylated erucic acid, polyethoxylated ricinoleic acid, polyethoxylated licanic acid, polyethoxylated elaeostearic acid, polyethoxylated arachidonic acid, polyethoxylated clupanodonic acid, polyethoxylated brasidic acid, hydroxpropyl laurate, hydroxypropyl myristate, hydroxypropyl palmitate, hydroxypropyl oleate, hydroxypropyl elaidate, hydroxypropyl linoleate, hydroxypropyl linolenate, hydroxypropyl stearate, hydroxypropyl erucate, hydroxypropyl ricinoleate, hydroxypropyl licanate, hydroxypropyl elaeostearate, hydroxypropyl arachidonate, hydroxypropyl clupanodonate, hydroxypropyl brasidate, polypropoxylated lauric acid, polypropoxylated myristic acid, polypropoxylated palmitic acid, polypropoxylated oleic acid, polypropoxylated elaidic acid, polypropoxylated linoleic acid, polypropoxylated linolenic acid, polypropoxylated stearic acid, polypropoxylated erucic acid, polypropoxylated ricinoleic acid, polypropoxylated licanic acid, polypropoxylated elaeostearic acid, polypropoxylated arachidonic acid, polypropoxylated clupanodonic acid, polypropoxylated brasidic acid, cyclopentyl laurate, cyclopentyl myristate, cyclopentyl palmitate, cyclopentyl oleate, cyclopentyl elaidate, cyclopentyl linoleate, cyclopentyl linolenate, cyclopentyl stearate, cyclopentyl erucate, cyclopentyl ricinoleate, cyclopentyl licanate, cyclopentyl elaeostearate, cyclopentyl arachidonate, cyclopentyl clupanodonate, cyclopentyl brasidate, cyclohexyl laurate, cyclohexyl myristate, cyclohexyl palmitate, cyclohexyl oleate, cyclohexyl elaidate, cyclohexyl linoleate, cyclohexyl linolenate, cyclohexyl stearate, cyclohexyl erucate, cyclohexyl ricinoleate, cyclohexyl licanate, cyclohexyl elaeostearate, cyclohexyl arachidonate, cyclohexyl clupanodonate, cyclohexyl brasidate, methoxyethyl laurate, methoxyethyl myristate, methoxyethyl palmitate, methoxyethyl oleate, methoxyethyl elaidate, methoxyethyl linoleate, methoxyethyl linolenate, methoxyethyl stearate, methoxyethyl erucate, methoxyethyl ricinoleate, methoxyethyl licanate, methoxyethyl elaeostearate, methoxyethyl arachidonate, methoxyethyl clupanodonate, methoxyethyl brasidate, isopropoxyethyl laurate, isopropoxyethyl myristate, isopropoxyethyl palmitate, isopropoxyethyl oleate, isopropoxyethyl elaidate, isopropoxyethyl linoleate, isopropoxyethyl linolenate, isopropoxyethyl stearate, isopropoxyethyl erucate, isopropoxyethyl ricinoleate, isopropoxyethyl licanate, isopropoxyethyl elaeostearate, isopropoxyethyl arachidonate, isopropoxyethyl clupanodonate, isopropoxyethyl brasidate, butoxyethyl laurate, butoxyethyl myristate, butoxyethyl palmitate, butoxyethyl oleate, butoxyethyl elaidate, butoxyethyl linoleate, butoxyethyl linolenate, butoxyethyl stearate, butoxyethyl erucate, butoxyethyl elaeostearate, butoxyethyl licanate, butoxyethyl ricinoleate, butoxyethyl arachidonate, butoxyethyl clupanodonate, butoxyethyl brasidate, methoxypropyl laurate, methoxypropyl myristate, methoxypropyl palmitate, methoxypropyl oleate, methoxypropyl elaidate, methoxypropyl linoleate, methoxypropyl linolenate, methoxypropyl stearate, methoxypropyl erucate, methoxypropyl ricinoleate, methoxypropyl licanate, methoxypropyl elaeostearate, methoxypropyl arachidonate, methoxypropyl clupanodonate, methoxypropyl brasidate, ethoxypropyl laurate, ethoxypropyl myristate, ethoxypropyl palmitate, ethoxypropyl oleate, ethoxypropyl elaidate, ethoxypropyl linoleate, ethoxypropyl linolenate, ethoxypropyl stearate, ethoxypropyl erucate, ethoxypropyl ricinoleate, ethoxypropyl licanate, ethoxypropyl elaeostearate, ethoxypropyl arachidonate, ethoxypropyl clupanodonate, ethoxypropyl brasidate, butoxypropyl laurate, butoxypropyl myristate, butoxypropyl palmitate, butoxypropyl oleate, butoxypropyl elaidate, butoxypropyl linoleate, butoxypropyl linolenate, butoxypropyl stearate, butoxypropyl erucate, butoxypropyl ricinoleate, butoxypropyl licanate, butoxypropyl elaeostearate, butoxypropyl arachidonate, butoxypropyl clupanodonate, butoxypropyl brasidate, isopropoxypropyl laurate, isopropoxypropyl myristate, isopropoxypropyl palmitate, isopropoxypropyl oleate, isopropoxypropyl telaidate, isopropoxypropyl linoleate, isopropoxypropyl linolenate, isopropoxypropyl stearate, isopropoxypropyl erucate, isopropoxypropyl ricinoleate, isopropoxypropyl licanate, isopropoxypropyl elaeostearate, isopropoxypropyl arachidonate, isopropoxypropyl clupanodonate, and isopropoxypropyl brasidate.

19. A method of performing ozonolysis on a molecule in a liquid as in claim 1 wherein said providing step comprises providing a composition consisting essentially of ozone and said liquid having an olefin molecule dissolved or dispersed in said liquid.

20. A method of performing ozonolysis on a molecule in a liquid as in claim 19 and wherein said liquid is liquid carbon dioxide.

21. A method of performing ozonolysis on a molecule in a liquid as in claim 1 wherein said providing step comprises providing a composition consisting of ozone and said liquid having an olefin molecule dissolved or dispersed in said liquid.

22. A method of performing ozonolysis on a molecule in a liquid as in claim 21 and wherein said liquid is liquid carbon dioxide.

23. A method of performing ozonolysis on a molecule in liquid carbon dioxide, the method comprising:
providing a composition having liquid carbon dioxide and ozone, wherein the liquid carbon dioxide and ozone composition has a temperature between about 0.9 to 1.35 times the critical temperature of ozone wherein the temperature is expressed in absolute units and a pressure above about 40.5 bar, wherein the molecule is dissolved or dispersed in the liquid carbon dioxide and such that the ozone is sharply compressed to selectively dissolve into the liquid carbon dioxide while background gases do not display a sham increase in compressibility; and
reacting the molecule with the ozone.

24. The method of performing ozonolysis as recited in claim 23, wherein said liquid carbon dioxide and ozone composition has a pressure between about 0.75 to about 1.5 times the critical pressure of ozone.

25. The method of performing ozonolysis as recited in claim 23, wherein said liquid carbon dioxide and ozone composition has a temperature between about 0.9 to about 1.35 times the critical temperature of ozone and a pressure between about 0.9 to about 1.35 times the critical pressure of ozone.

26. The method of performing ozonolysis as recited in claim 23, wherein said liquid carbon dioxide and ozone composition has a temperature between about 0.95 to about 1.25 times the critical temperature of ozone and a pressure between about 0.95 to about 1.25 times the critical pressure of ozone.

27. The method of performing ozonolysis as recited in claim 23, wherein said liquid carbon dioxide and ozone composition has a temperature between about 1 to about 1.15 times the critical temperature of ozone and a pressure between about 1 to about 1.15 times the critical pressure of ozone.

\* \* \* \* \*